United States Patent
Zlokovic et al.

(10) Patent No.: US 10,342,221 B2
(45) Date of Patent: Jul. 9, 2019

(54) GENERATION OF AN INDUCIBLE PERICYTE-SPECIFIC CRE MOUSE MODEL

(71) Applicant: University of Southern California, Los Angeles, CA (US)

(72) Inventors: Berislav Zlokovic, Los Angeles, CA (US); Zhen Zhao, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 15/681,150

(22) Filed: Aug. 18, 2017

(65) Prior Publication Data

US 2018/0049411 A1 Feb. 22, 2018

Related U.S. Application Data

(60) Provisional application No. 62/377,425, filed on Aug. 19, 2016.

(51) Int. Cl.
*A01K 67/00* (2006.01)
*A01K 67/027* (2006.01)

(52) U.S. Cl.
CPC .... *A01K 67/0275* (2013.01); *A01K 2217/075* (2013.01); *A01K 2217/15* (2013.01); *A01K 2217/203* (2013.01); *A01K 2217/206* (2013.01); *A01K 2227/105* (2013.01)

(58) Field of Classification Search
USPC .............................................. 800/3, 18, 21
See application file for complete search history.

(56) References Cited

U.S. PATENT DOCUMENTS

| | | | | |
|---|---|---|---|---|
| 8,124,829 | B2 * | 2/2012 | Stern | A01K 67/0275 800/13 |
| 9,718,878 | B2 * | 8/2017 | Lindner | A61K 38/1709 |
| 9,901,650 | B2 * | 2/2018 | Nedergaard | A61K 51/0491 |
| 2017/0304463 | A1 * | 10/2017 | Chen | A61K 38/1709 |

OTHER PUBLICATIONS

Ampofo (Cell Mol. Biol. Letters, 2017, vol. 22, No. 4, p. 1-9.*

* cited by examiner

*Primary Examiner* — Michael C Wilson
(74) *Attorney, Agent, or Firm* — Stephen W. Chen; Nixon Peabody LLP

(57) ABSTRACT

Pericytes are mural cells of brain capillaries that degenerate in multiple neurological disorders. Pericytes regulate neurovascular functions, but their role in the adult brain and disease is still poorly understood because of the lack of adequate pericyte-specific experimental models. All current pericyte-deficient models are not pericyte specific, and carry an inherited embryonic trait. Here, the Inventors generated an inducible pericyte-specific Cre line using a double-promoter strategy. The Inventors ablated adult mouse pericytes expressing Cre-dependent diphtheria toxin receptor after toxin administration. Pericyte ablation led to a rapid dysregulation of cerebral blood flow and blood-brain barrier breakdown. This was followed by behavioral deficits and neurodegenerative changes. These findings show that circulatory deficits leading to secondary neurodegeneration develop immediately after pericyte loss.

4 Claims, 15 Drawing Sheets

Specification includes a Sequence Listing.

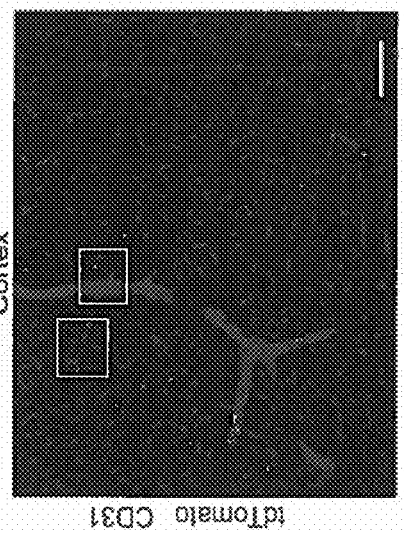
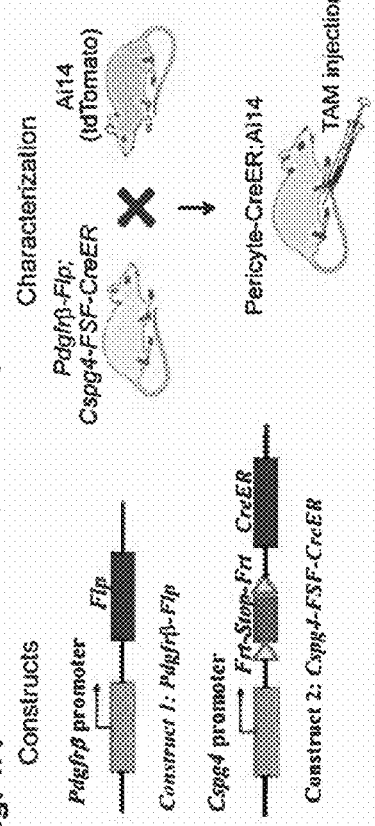
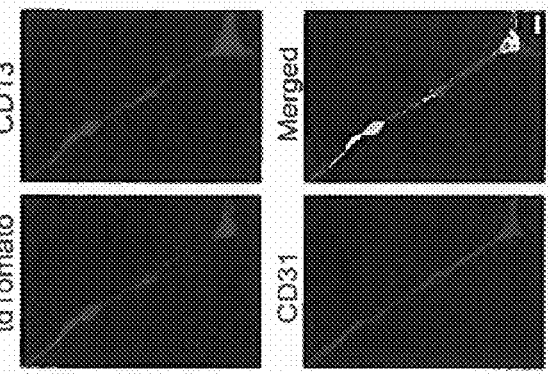
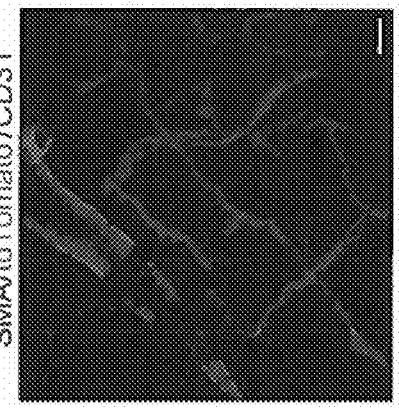
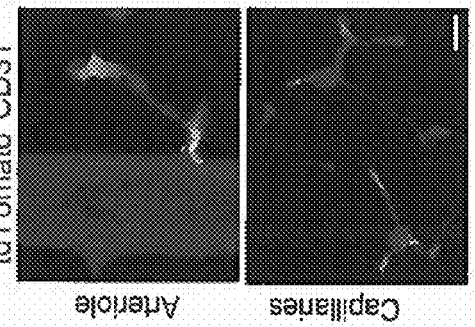

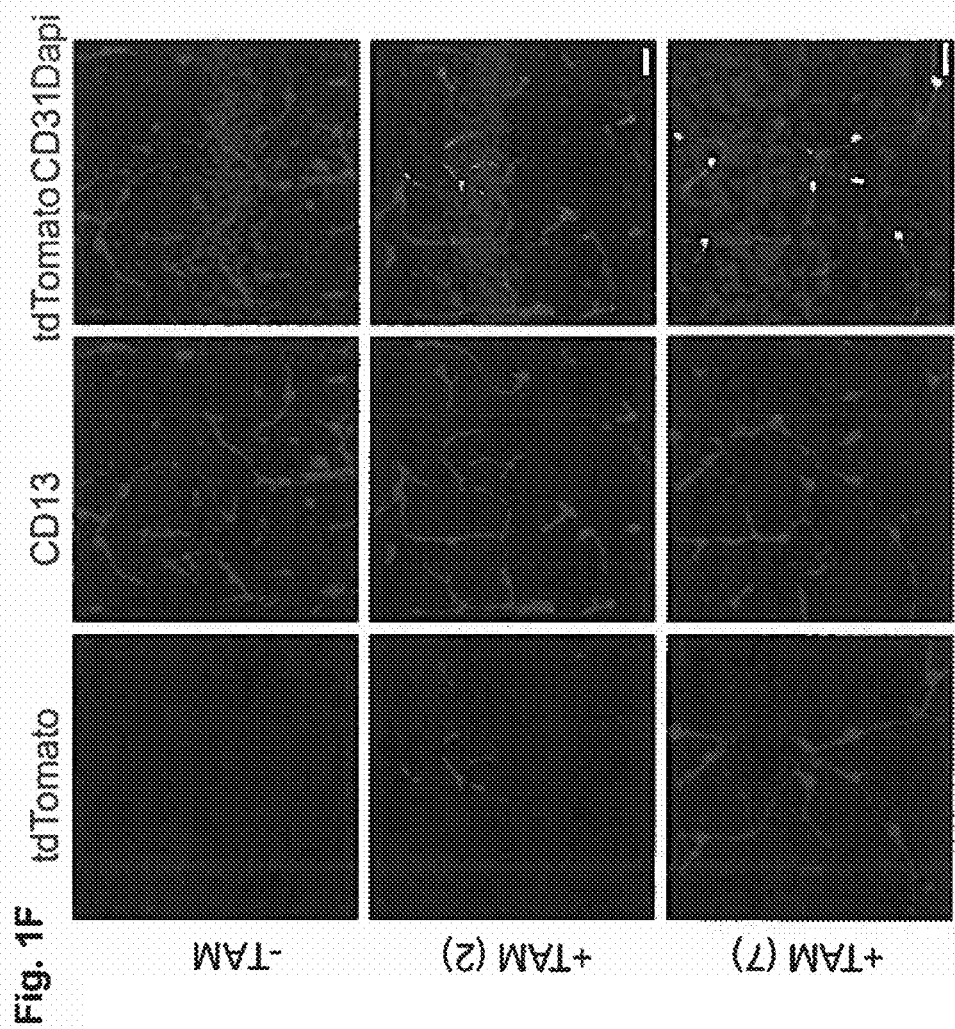

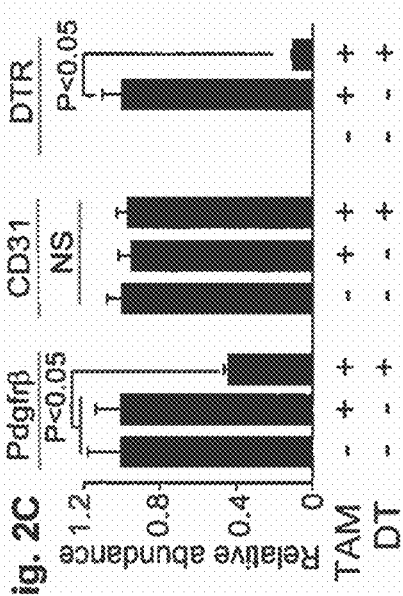
Fig. 2A
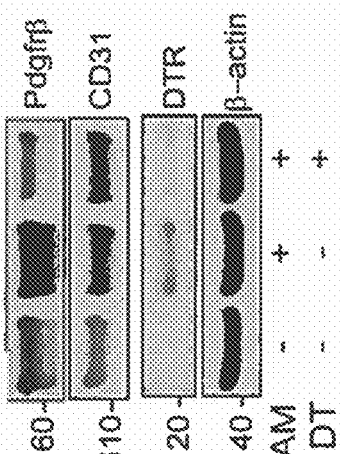
Fig. 2B
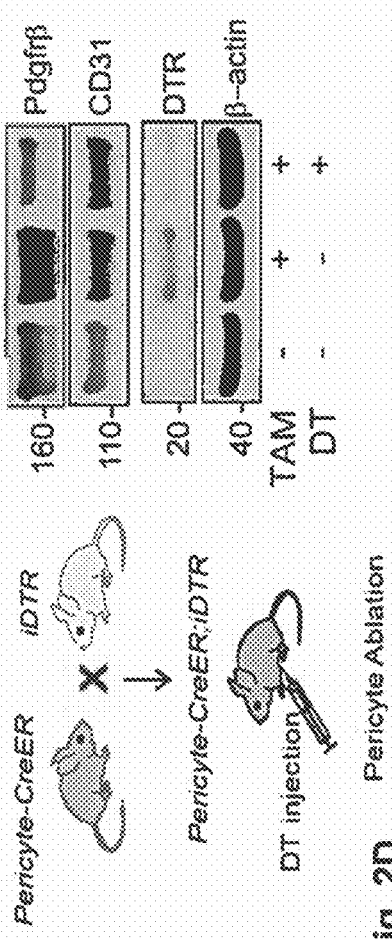
Fig. 2C
Fig. 2D
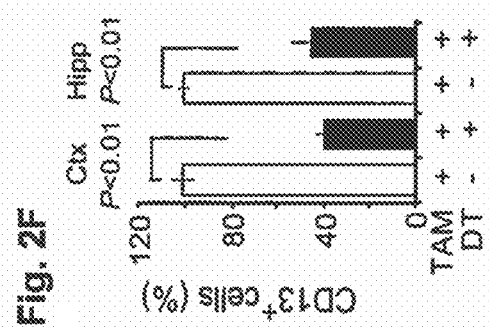
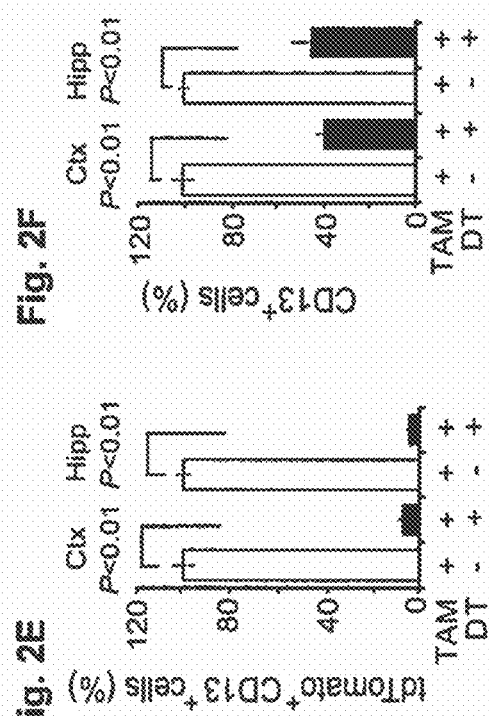
Fig. 2E
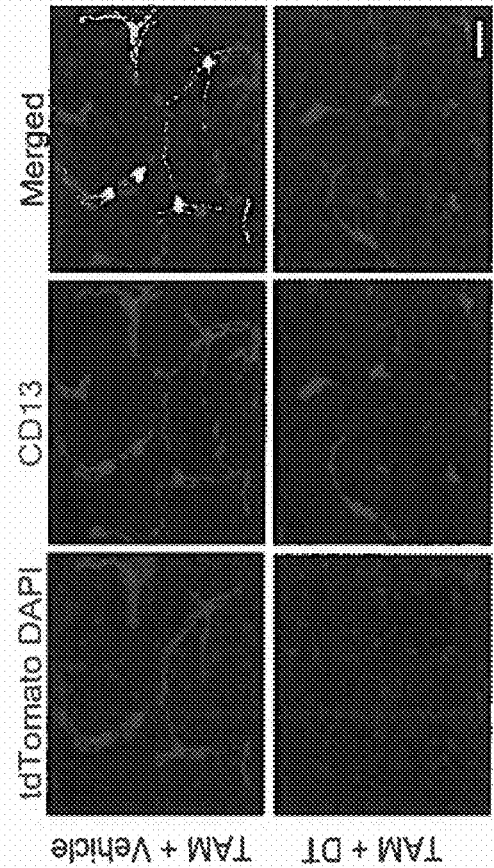
Fig. 2F

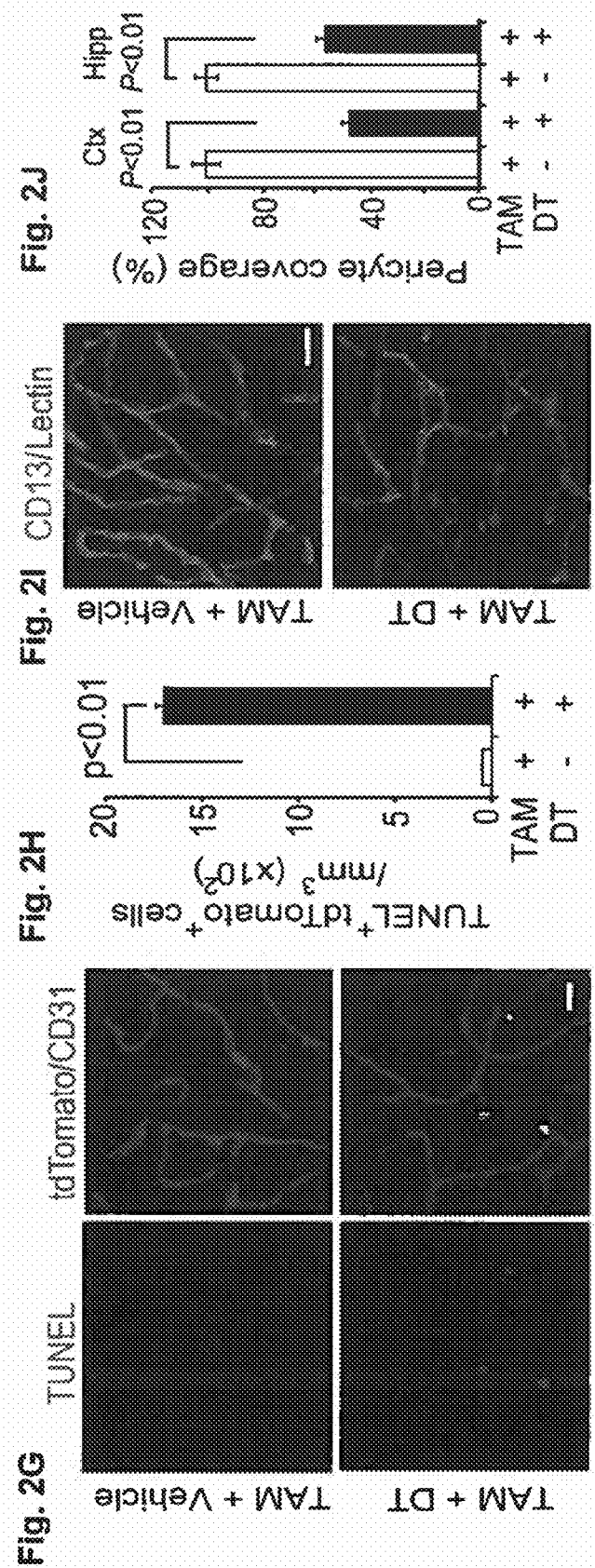

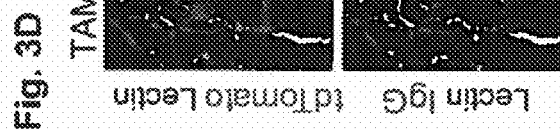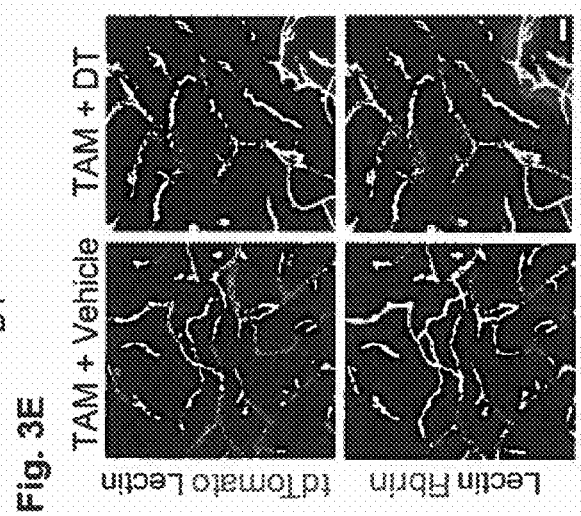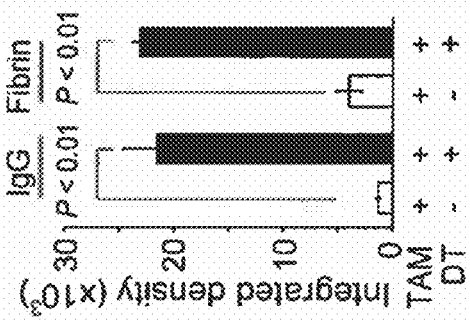

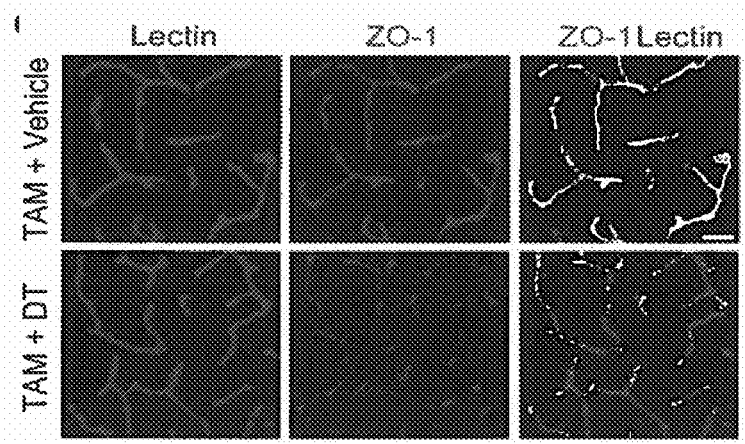
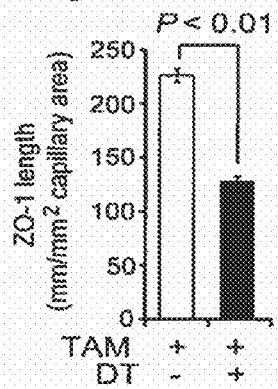
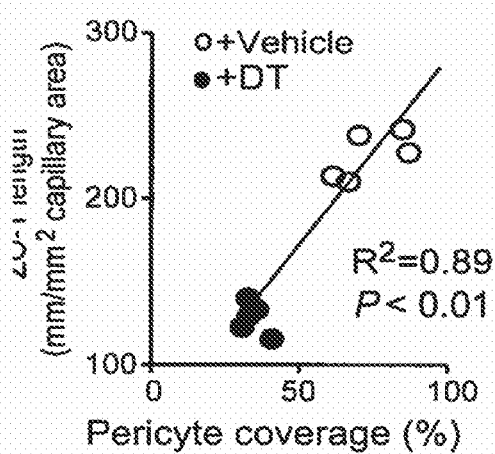
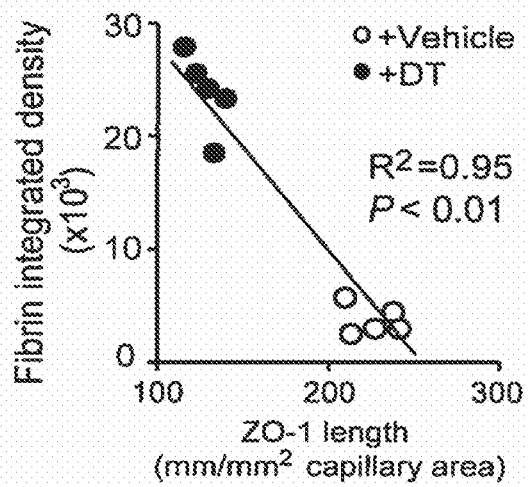

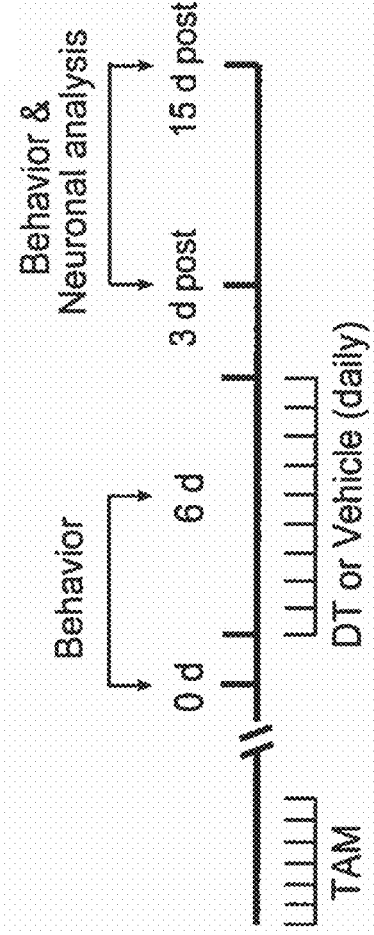
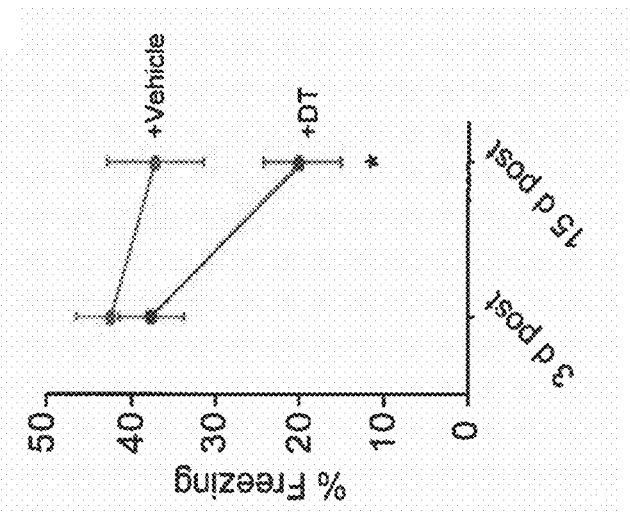
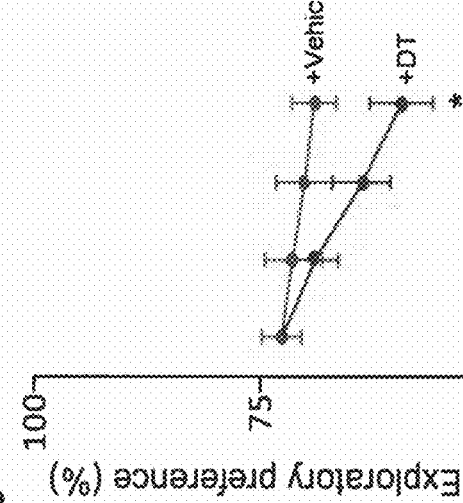
Fig. 4A
Fig. 4B
Fig. 4C

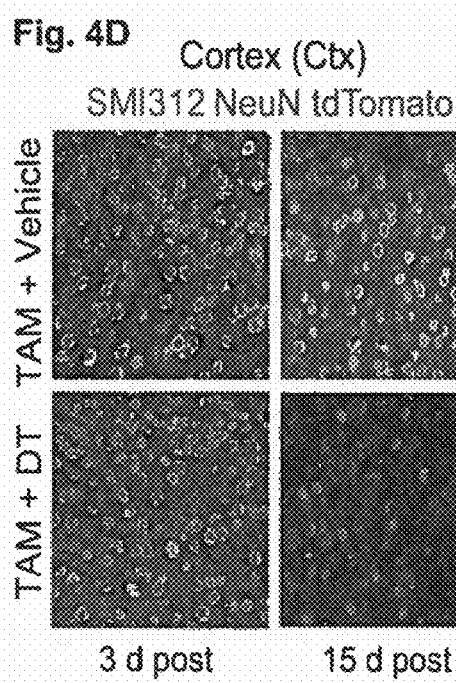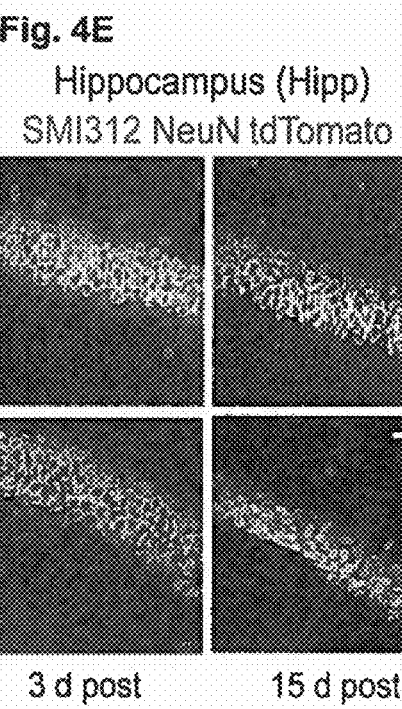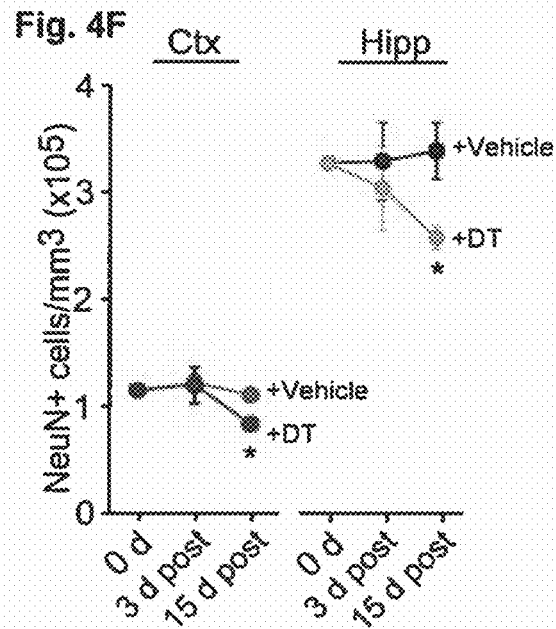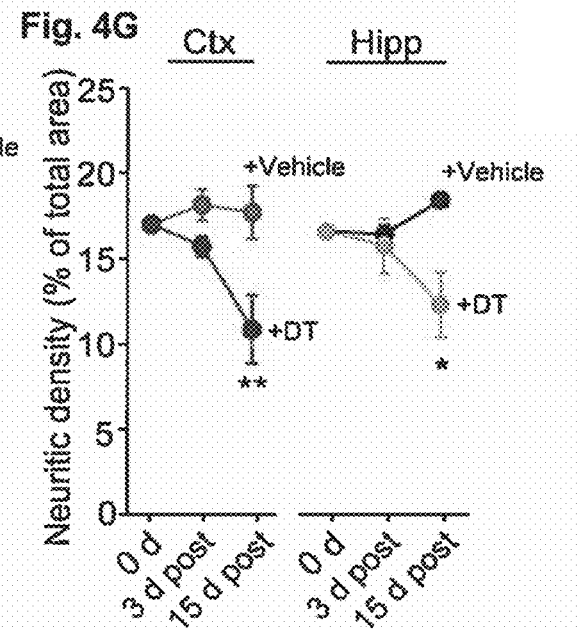

PDGFRβ Olig2 Lectin

PDGFRβ NG2 SMA

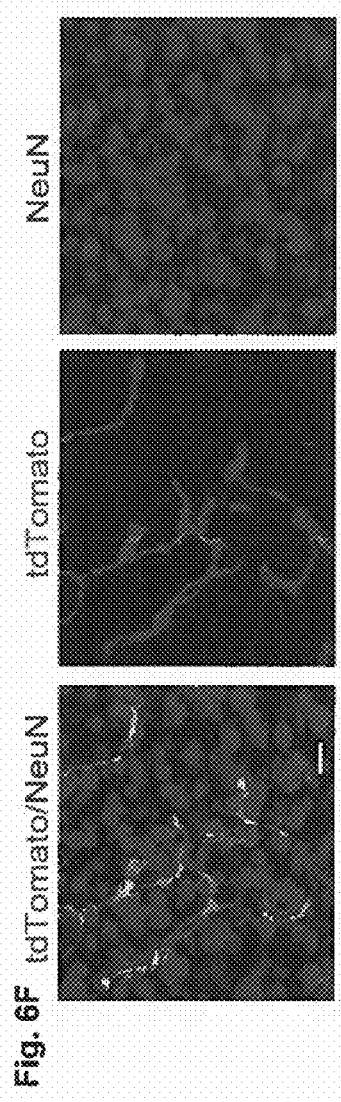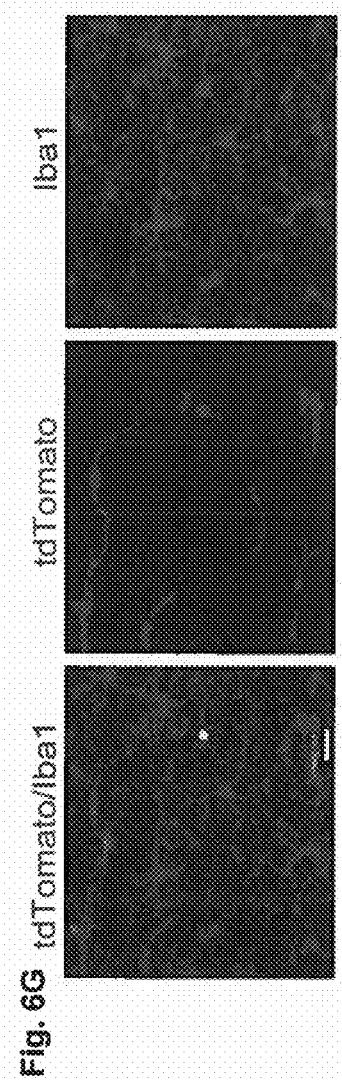
Fig. 6D tdTomato/GFAP    Fig. 6E tdTomato    Fig. 6F tdTomato/NeuN    Fig. 6G tdTomato/Iba1

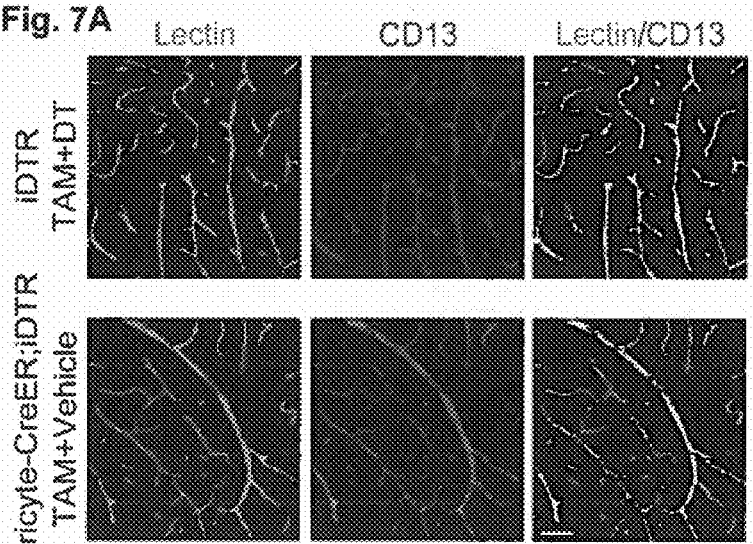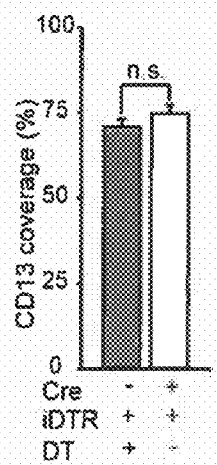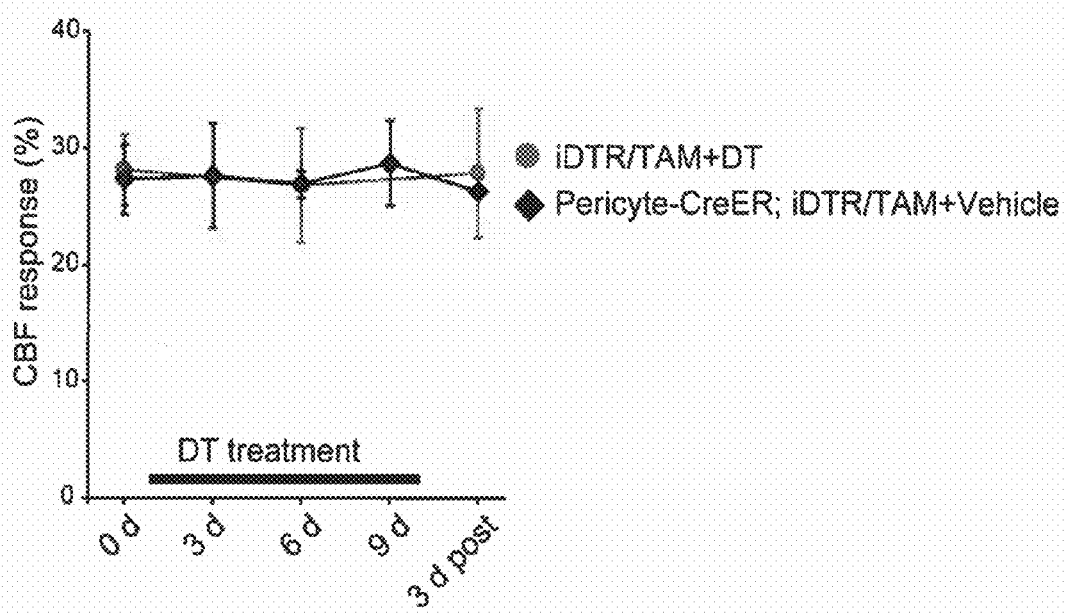

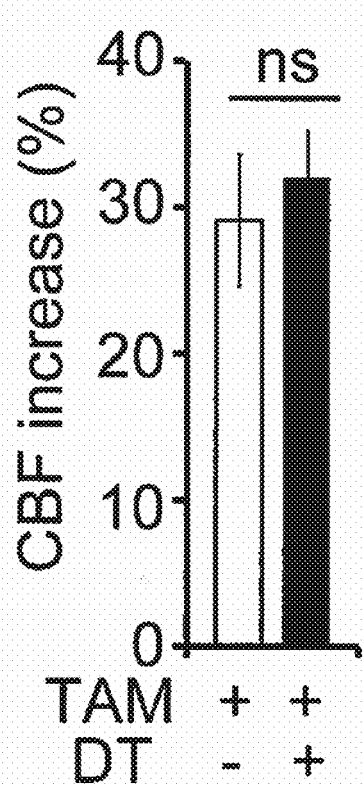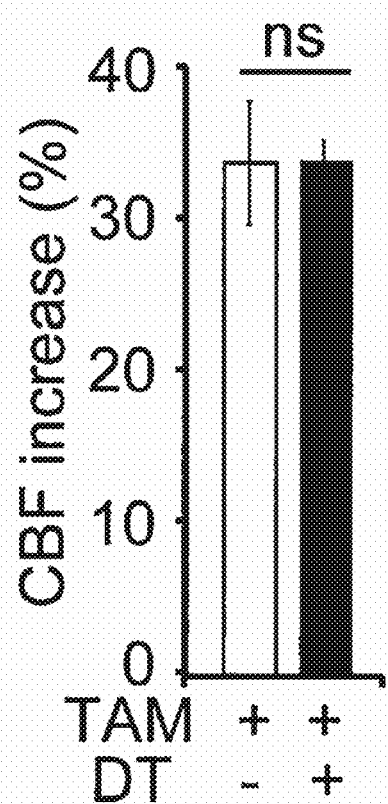

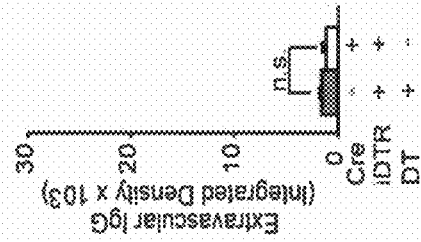
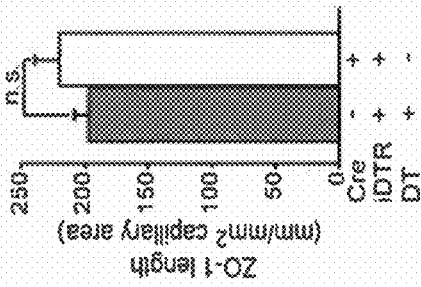
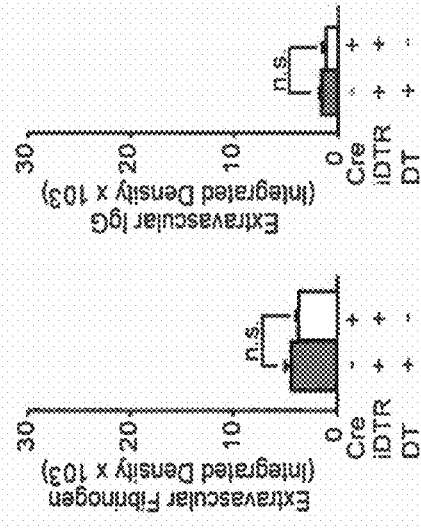
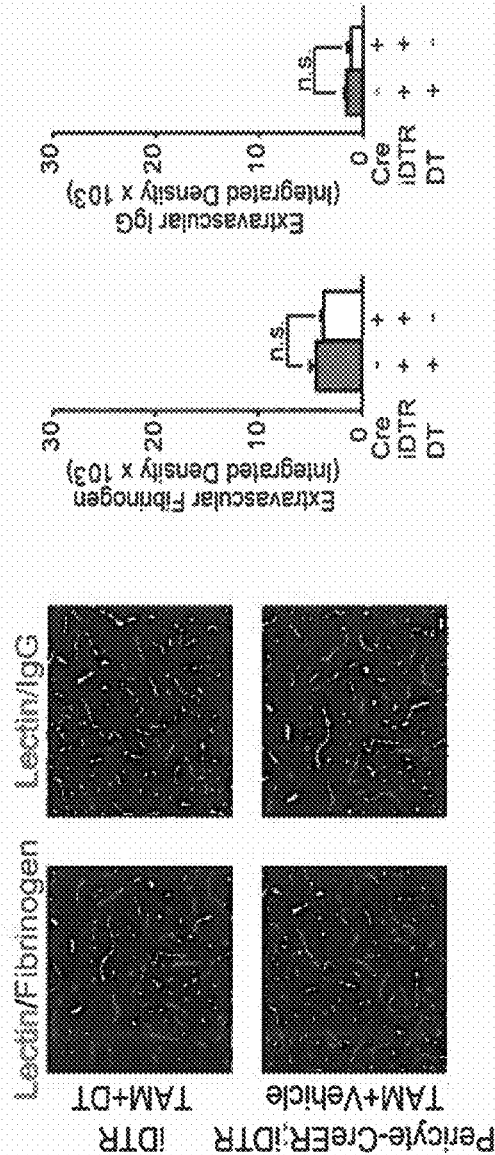
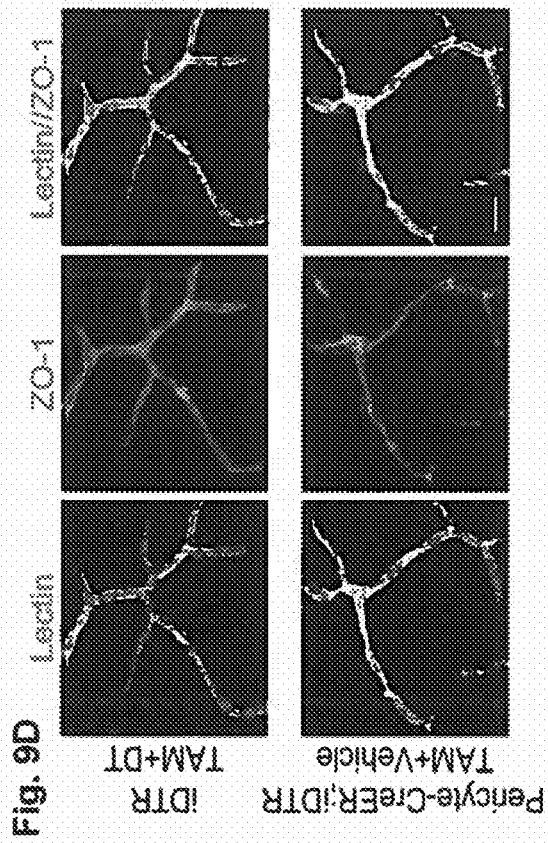

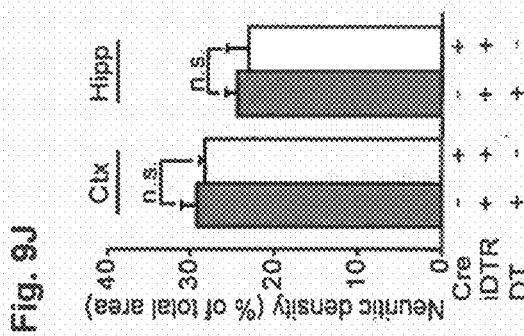
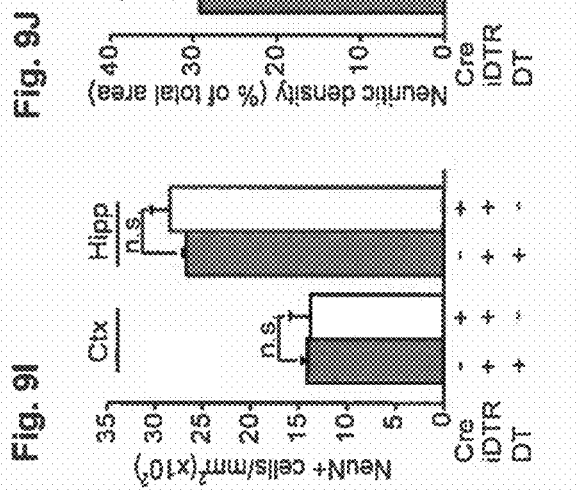
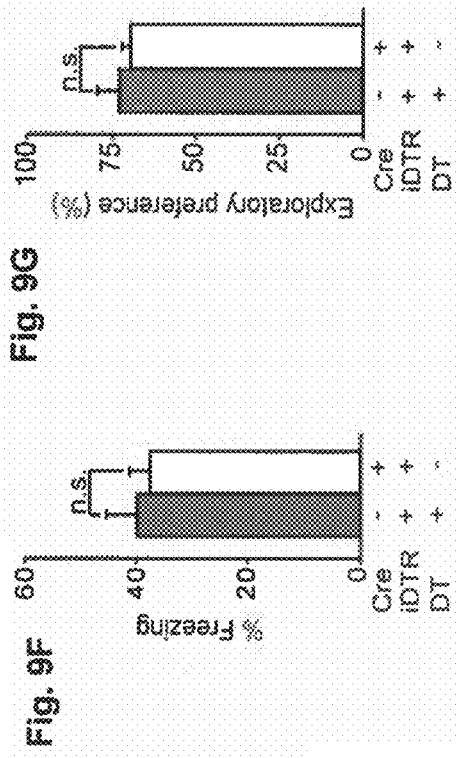
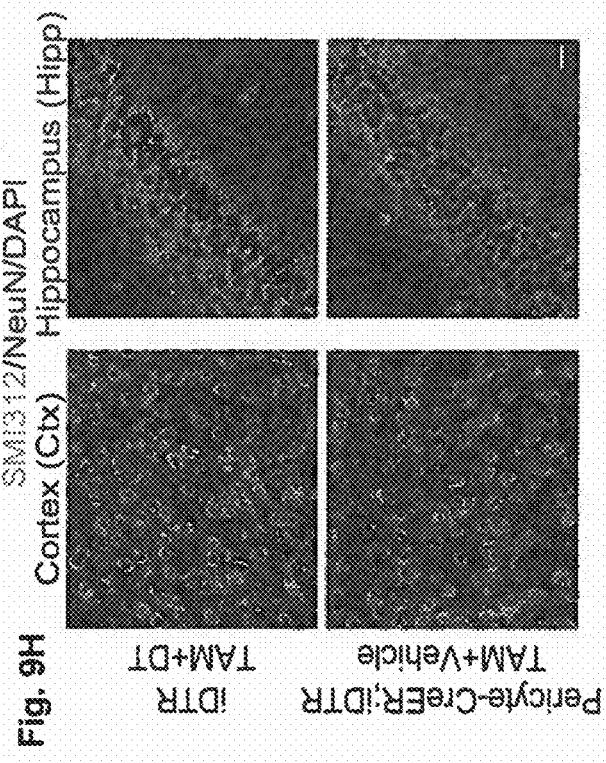

GENERATION OF AN INDUCIBLE PERICYTE-SPECIFIC CRE MOUSE MODEL

STATEMENT REGARDING FEDERALLY SPONSORED RESEARCH OR DEVELOPMENT

This Invention was made with government support under Grant No. AG039452 awarded by the National Institutes of Health. The government has certain rights in the invention.

FIELD OF THE INVENTION

This invention relates to vascular cells and neuroscience, specifically pericityes.

BACKGROUND

Pericytes are vascular mural cells embedded in the basement membrane of blood microvessels. They extend their processes along the walls of brain capillaries, pre-capillary arterioles, and post-capillary venules. Pericytes are situated centrally within the neurovascular unit between brain endothelial cells, astrocytes and neurons. This unique position allows them to process and respond to signals from their neighboring cells generating functional responses that are critical for different central nervous system (CNS). Pericyte injury and/or degeneration are found in multiple neurological disorders exhibiting neurovascular dysfunction and BBB breakdown. However, the exact role of pericyte dysfunction and loss in the pathogenesis of these disorders remains at present unclear.

Studies in pericyte-deficient mouse models have been carried out almost exclusively in transgenic animals with embryonically disrupted angiogenic signaling between endothelial-derived platelet-derived growth factor BB (PDGF-BB) and platelet-derived growth factor receptor β (PDGFRβ) in pericytes. Albeit extremely useful for understanding pericyte biology and providing important initial insights into their role in regulating neurovascular functions, models of PDGF-BB and PDGFRβ deficiency are not pericyte specific. They cannot isolate the potential contribution of other PDGFRβ-expressing CNS cell types, or the developmental impact of embryonic loss of PDGFRβ signaling on neurovascular and possibly neuronal phenotype that develops later in adult life and aging brain. For instance, in addition to pericytes, vascular smooth muscle cells (VSMCs) express also PDGFRβ, and some studies suggest that even cultured neurons and embryonic neurons express PDGFRβ, although not confirmed in the embryonic CNS or adult brain by others.

Described herein is an inducible pericyte-specific Cre line using a double-promoter strategy. The Inventors ablated adult mouse pericytes expressing Cre-dependent diphtheria toxin receptor after toxin administration. Pericyte ablation led to a rapid dysregulation of cerebral blood flow and blood-brain barrier breakdown. This was followed by behavioral deficits and neurodegenerative changes. These findings show that circulatory deficits leading to secondary neurodegeneration develop immediately after pericyte loss. These data indicate that pericyte degeneration as seen in neurological disorders with neurovascular dysfunction can contribute to neurodegeneration, suggesting new therapeutic strategies focusing on this particular cell type.

BRIEF DESCRIPTION OF FIGURES

FIG. 1. Generation and characterization of pericyte-specific Cre line using double promoter strategy. (FIG. 1A) Left. A schematic diagram of the two constructs, SEQ ID NO:1 and SEQ ID NO:2, used to generate pericyte-specific Cre mouse line: the Pdgfrb promoter to express Flippase (Flp) (SEQ ID NO:1) and the Cspg4 promoter to drive the Frt-Stop-Frt-CreER cassette (SEQ ID NO:2) (See methods). Right. To characterize Cre expression pattern, Pdgfrβ-Flp; Cspg4-FSF-CreER mice were crossed with the Ai14 tdTomato reporter line generated with SEQ ID NO: 3. (FIG. 1B, FIG. 1C, FIG. 1D, FIG. 1E) Characterization of Pdgfrβ-Flp; Cspg4-FSF-CreER mice crossed with the Ai14 reporter mice expressing tdTomato. (FIG. 1B) A low magnification image showing expression of tdTomato in perivascular mural cells of brain microvessels in the primary somatosensory cortex of Pdgfrβ-Flp; Cspg4-FSF-CreER mice crossed with the Ai14 reporter mice 2 weeks after tamoxifen treatment (TAM, 4 injections, 40 mg/kg, i.p., see methods). Bar=50 μm. (FIG. 1C). Representative images from the boxed region in FIG. 1B showing restricted tdTomato expression in perivascular mural cells of brain capillaries (<6 mm in diameter). Bar=20 μm. (FIG. 1D) A representative image showing that tdTomato is not expressed in SMA (smooth muscle actin)-positive vascular smooth muscle cells of the arteriolar wall in the cortex of Pdgfrβ-Flp; Cspg4-FSF-CreER mice crossed with the Ai14 reporter mice 2 weeks after TAM treatment (4 injections, 40 mg/kg i.p.). Bar=20 μm. (FIG. 1E) Colocalization of Cre-driven tdTomato with CD13 (green), a pericyte marker, but not CD31, a marker of brain endothelial cells in the cortex of Pdgfrβ-Flp; Cspg4-FSF-CreER mice crossed with the Ai14 reporter mice 2 weeks after TAM treatment (4 injections, 40 mg/kg i.p.). Bar=10 μm. (FIG. 1F, FIG. 1G) Representative confocal images of tdTomato+ and CD13+ double-positive pericytes in the CA1 (upper and middle panels) and CA3 (lower panel) hippocampus subfields (FIG. 1F), and quantification (FIG. 1G) of tdTomato+ and CD13+ double-positive pericytes in the hippocampus (20 randomly chosen fields from 5 non-adjacent hippocampus section per mouse) of Pdgfrβ-Flp; Cspg4-FSF-CreER mice crossed with the Ai14 reporter mice treated with 2, 4 and 7 TAM injections (40 mg/kg i.p. per injection). Dapi, nuclear staining. Staining was performed 2 weeks after TAM treatment. In FIG. 1G, Mean±S.E.M, n=5 mice per group. Bars=20 μm. P<0.05, ANOVA followed by Bonferroni posthoc test.

FIG. 2. Inducible pericyte ablation in pericyte-CreER; iDTR mice treated with diphtheria toxin. (FIG. 2A) Animal breeding strategy to develop mice with inducible pericyte ablation using Pericyte-CreER mice from FIG. 1 crossed with iDTR mice. (FIG. 2B, FIG. 2C) Representative immunoblotting (FIG. 2B) and quantification (FIG. 2C) of pericyte biomarker PDGFRb, endothelial biomarker CD31 and DTR levels in brain capillaries (<6 mm in diameter) isolated from 3 month old pericyte-CreER; iDTR mice treated with vehicle or tamoxifen (TAM, 7 consecutive injections, 40 mg/kg, i.p.) followed by administration of diphtheria toxin (DT) (i.p., 1 mg/day for 10 days) or vehicle 2 weeks after TAM. Brain capillaries were isolated 3 days after the last DT or vehicle injection. Mean±S.E.M., n=3 mice per group. P<0.05, ANOVA followed by Bonferroni posthoc test. (FIG. 2D, FIG. 2E, FIG. 2F) Representative confocal images of tdTomato$^+$ and CD13$^+$ double-positive pericytes in the primary somatosensory cortex (Ctx) (FIG. 2D) and quantification of tdTomato$^+$ and CD13$^+$ double-positive pericytes (FIG. 2E) and CD13$^+$ pericyte cell bodies (FIG. 2F) in the cortex and the CA1 hippocampus subfield (Hipp) in 3-month-old pericyte-CreER; iDTR mice treated with vehicle or TAM followed by DT or vehicle treatment 2 weeks after TAM as in C. Tissue analysis was performed 3 days after the last DT or vehicle injection. Mean±S.E.M., n=5 mice per group. P<0.05, Student's t-test. Bar=20 µm. (FIG. 2G, FIG. 2H) Representative confocal images of TUNEL⁺ and tdTomato⁺ double-positive cells in the cortex (FIG. 2G) and quantification of TUNEL⁺ and tdTomato⁺ double-positive cells in the cortex of 3-month-old pericyte-CreER; iDTR mice treated with vehicle or TAM followed by DT or vehicle as in FIG. 2C. Tissue analysis was performed 3 days after the last DT or vehicle injection. CD31, endothelial marker; bar=20 µm. Mean±S.E.M, n=5 mice per group. P<0.05, Student's t-test. (FIG. 2I, FIG. 2J) Representative confocal images of CD13⁺ pericyte coverage of lectin⁺ endothelial profiles in the cortex (FIG. 2I) and quantification of CD13⁺ pericyte coverage of lectin⁺ endothelial microvascular profiles (FIG. 2J) in the cortex and hippocampus in 3-month-old pericyte-CreER; iDTR mice treated with vehicle or TAM followed by DT or vehicle as in C. Tissue analysis was performed 3 days after the last DT or vehicle injection. Bar=20 µm. Mean±S.E.M., n=5 mice per group. P<0.05, Student's t-test.

FIG. 3. Cerebral blood flow dysregulation and blood-brain barrier breakdown in pericyte-CreER; iDTR mice treated with diphtheria toxin. (FIG. 3A) A protocol of tamoxifen (TAM, 7 consecutive injections, 40 mg/kg, i.p.) and diphtheria toxin (DT) (1 µg per day for 10 consecutive days) or vehicle administration in pericyte-CreER; iDTR mice. DT or vehicles were administered 2 weeks after TAM. Cerebral blood flow (CBF) responses were measured before and 3 days after DT or vehicle treatment. The blood-brain barrier (BBB) integrity was assessed by tissue analysis 3 days after DT or vehicle treatment. (FIG. 3B) CBF responses to an electrical hind limb stimulus (60 s, 7 Hz, 2 ms pulse duration) were measured by laser Doppler flowmetry and expressed as a percentage of baseline change on day 0 (before DT) and 3 days after DT or vehicle treatment (3 d post) in 3-month old pericyte-CreER; iDTR mice treated as shown in A. Mean±S.E.M., n=5 mice per group; ns, non-significant; P<0.05, ANOVA followed by Bonferroni post-hoc test. (FIG. 3C) Pearson's correlation plot between CBF responses and pericyte coverage in 10 individual mice studied in B. The analysis was performed 3 days after DT or vehicle treatment. (FIG. 3D, FIG. 3E, FIG. 3F) Representative confocal images (FIG. 3D, FIG. 3E) and quantification (FIG. 3F) showing extravasation of plasma-derived IgG (red, FIG. 3D, FIG. 3F) and fibrin (red, FIG. 3E, FIG. 3F) in the primary somatosensory cortex of 3-month old pericyte-CreER; iDTR mice treated with DT or vehicle as shown in FIG. 3B. Tissue was analyzed 3 days after DT or vehicle treatment. Lectin⁺ microvessels are shown in white; tdTomato⁺ pericytes are shown in magenta. Bar=20 µm. Mean±S.E.M, n=5 mice per group, P<0.05, Student's t-test. (FIG. 3G, FIG. 3H) Representative confocal images of tight junction protein ZO-1 and lectin+ endothelial profiles (FIG. 3G) and quantification of ZO-1 length within the microvascular lectin⁺ brain endothelial profiles (FIG. 3H) in the cortex of 3-month old pericyte-CreER; iDTR mice treated with DT or vehicle. Tissue analysis was performed 3 days after DT or vehicle treatment. Bar=20 µm. Mean±S.E.M., n=5 mice per group. P<0.05, Student's t-test. (FIG. 3I, FIG. 3J) Pearson's correlation plots between pericyte coverage and ZO-1 length (FIG. 3I), and ZO-1 length and extravascular fibrin deposits (FIG. 3J) in 10 individual mice studied in FIG. 3D, Fig. FIG. 3E, FIG. 3F, FIG. 3G, FIG. 3H. The analysis was performed 3 days after DT or vehicle treatment.

FIG. 4. Behavioral deficits and neurodegeneration in pericyte-CreER; iDTR mice treated with diphtheria toxin. (FIG. 4A) A protocol of tamoxifen (TAM, 7 consecutive injections, 40 mg/kg, i.p.), and diphtheria toxin (DT) (1 µg per day for 10 consecutive days) or vehicle administration in pericyte-CreER; iDTR mice. DT or vehicle was administered 2 weeks after TAM. Behavioral tests and tissue analysis (i.e., neuron numbers and neuritic density) were performed before and after DT or vehicle treatment as indicated. (FIG. 4B) Novel object location test in 3 month old pericyte-CreER; iDTR mice treated as shown in FIG. 4A. Test was performed before DT or vehicle treatment (0 d), 6 days during DT or vehicle treatment (6 d), and 3 and 15 days after DT or vehicle treatment (3 and 15 d post). (FIG. 4C) Fear conditioning test in 3 month old pericyte-CreER; iDTR mice treated as shown in FIG. 4A 3 and 15 days after DT or vehicle treatment (3 and 15 d post). In FIG. 4B and FIG. 4C, mean±S.E.M., n=6-15 mice per group, P<0.05, ANOVA followed by Bonferroni posthoc test. (FIG. 4D, FIG. 4E, FIG. 4F, FIG. 4G) Representative confocal images (FIG. 4D, FIG. 4E) and quantification (FIG. 4F, FIG. 4G) of the number of NeuN⁺ neurons (green, FIG. 4D, FIG. 4F) and SMI312⁺ neuritic density of (red, FIG. 4E, FIG. 4G) in the primary somatosensory cortex (Ctx, FIG. 4D, FIG. 4F, FIG. 4G) and the CA1 hippocampus subfield (Hipp, FIG. 4E, FIG. 4F, FIG. 4G) on day 0 before treatment, and 3 and 15 days after DT or vehicle treatment (3 and 15 d post) in 3-month old pericyte-CreER; iDTR mice treated as shown in FIG. 4A. Bar=50 µm. Mean±SD; n=5 mice per group; P<0.05, ANOVA followed by Bonferroni posthoc test.

FIG. 5: Two-promoter strategy for generating the Pericyte-Cre mice. In FIG. 5D, FIG. 5E, representative images from 3 independent experiments; Bars=50 µm.

FIG. 6. Characterization of the pericyte-Cre; Ai14 mouse line. (FIG. 6D, FIG. 6E) Representative confocal images showing that tdTomato is not expressed in GFAP⁺ astrocytes. FIG. 6E, high magnification of boxed region in FIG. 6D, and orthogonal view (right panel) showing that a tdTomato$^+$ pericyte is in close proximity, but not overlap with the adjacent GFAP$^+$ cell. Bar=20 µm. (FIG. 6F) Representative confocal images showing that tdTomato is not expressed in NeuN$^+$ cortical neurons. Bar=20 µm. (FIG. 6G) Representative confocal images showing that tdTomato is not expressed in Iba1$^+$ resident microglia. Bar=20 µm. Representative images were obtained from the primary somatosensory cortex of 3 independent animals sacrificed two weeks after tamoxifen treatment (TAM, 7 consecutive injections, 40 mg/kg, i.p). Tissue analyses were performed 2 weeks after TAM treatment.

FIG. 7. Diphtheria toxin administration does not alter pericyte coverage and cerebral blood flow response in control iDTR mice treated with TAM and vehicle compared to vehicle and TAM-treated pericyte-CreER; iDTR mice. (FIG. 7A, FIG. 7B) Representative confocal images (FIG. 7A) and quantification of pericyte coverage (FIG. 7B) in iDTR animals treated with tamoxifen (TAM, 40 mg/kg i.p. for 7 consecutive days) and DT (1 µg per day for 10 consecutive days) two weeks after TAM as in FIG. 3, showing no changes in pericyte coverage in the primary somatosensory cortex 3 days after DT treatment when compared to vehicle and TAM-treated pericyte-CreER; iDTR mice 3 days after vehicle treatment. iDTR, ROSA26iDTR with Cre-inducible expression of DTR. Bar=20 µm. Mean±S.E.M.; n=5 mice per group; ns, nonsignificant, by Student's t-test. (FIG. 7C) Cerebral blood flow (CBF) responses to an electrical hind limb stimulus (60 s, 7 Hz, 2 ms pulse duration) determined by laser doppler flowmetry (LDF) in TAM treated iDTR animals on 0, 3, 6 and 9 days during the DT treatment (3 d, 6 d, 9 d) and 3 days after DT treatment (3 d post), showing no change in baseline compared to vehicle and TAM-treated pericyte-CreER; iDTR mice. Mean±S.E.M.; n=5 mice per group; ns, nonsignificant, by ANOVA followed by Bonferroni posthoc test. Representative images were obtained from the primary somatosensory cortex of 3 independent animals.

FIG. 8. Pericyte ablation in pericyte-CreER; iDTR mice does not alter endothelial or smooth muscle cell-dependent blood flow response. (FIG. 8A, FIG. 8B) Laser Doppler flowmetry measurements of in vivo cerebral blood flow (CBF) responses to endothelium-dependent vasodilator acetylcholine (10 µM) (FIG. 8A) and endothelium-independent vascular smooth muscle cell relaxant adenosine (400 µM) (FIG. 8B) in 3-month old pericyte-CreER; iDTR mice that received TAM (7 injections, 40 mg/kg, i.p.) followed by DT (1 µg per day for 10 consecutive days, as in FIG. 3) or vehicle treatment. The CBF responses were determined 3 days after DT or vehicle treatment. Mean±S.E.M.; n=5 mice per group; ns, nonsignificant, by Student's t-test.

FIG. 9. Diphtheria toxin administration does not alter cerebrovascular integrity and neuronal health in control iDTR mice treated with TAM and vehicle compared to vehicle and TAM-treated pericyte-CreER; iDTR mice. (FIG. 9A-C) Representative confocal images (FIG. 9A) and quantification of extravascular fibrin (FIG. 9B) and IgG (FIG. 9C), show no detectable BBB leakage in the primary somatosensory cortex of TAM and DT-treated iDTR animals 3 days after DT treatment, compared to TAM-treated pericyte-CreER; iDTR mice 3 days after vehicle treatment. Bar=20 µm. Mean±S.E.M.; n=5 mice per group; ns, nonsignificant, by Student's t-test. (FIG. 9D-FIG. 9E) Representative confocal images (FIG. 9D) and quantification of ZO-1 tight junction protein length (FIG. 9E) in the primary somatosensory cortex of TAM-treated iDTR animals 3 days after DT treatment as in FIG. 9A, showing no changes compared to TAM-treated pericyte-CreER; iDTR mice 3 days after vehicle treatment. Bar=20 µm. Mean±S.E.M.; n=5 mice per group; ns, nonsignificant, by Student's t-test. (FIG. 9F-FIG. 9G) Behavioral studies in TAM and DT-treated iDTR animals showing no difference in fear conditioning (FIG. 9F) or novel object location test (FIG. 9G) when compared to TAM-treated pericyte-CreER; iDTR mice after vehicle treatment. Mean±S.E.M.; n=5 mice per group; ns, nonsignificant, by Student's t-test. (FIG. 9H, FIG. 9I, FIG. 9J) Confocal images (FIG. 9H) and quantification of NeuN$^+$ cells (FIG. 9I) and SMI312$^+$ neuritic density (FIG. 9J) in the primary somatosensory cortex (Ctx) and CA1 hippocampus subfield (Hipp) of TAM and DT-treated iDTR animals showing no neuronal changes when compared to TAM-treated pericyte-CreER; iDTR mice after vehicle treatment. Bar=20 µm. Mean±S.E.M.; n=5 mice per group; ns, nonsignificant, by Student's t-test.

DETAILED DESCRIPTION

Figure 5A:
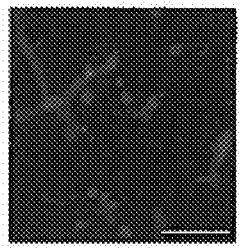
(FIG. 5A) Confocal microscopy image showing that OLIG2 (green), a marker of oligodendrocytes including oligodendrocyte precursor cells (OPCs), does not colocalize with PDGFRβ-positive pericytes (magenta) on lectin-positive capillary profiles (blue) in the cortex of 3 month old C57BL/6 wild type mice.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., Reshaping human antibodies for therapy, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Pericytes are vascular mural cells embedded in the basement membrane of blood microvessels. They extend their processes along the walls of brain capillaries, pre-capillary arterioles, and post-capillary venules. Pericytes are situated centrally within the neurovascular unit between brain endothelial cells, astrocytes and neurons. This unique position allows them to process and respond to signals from their neighboring cells generating functional responses that are critical for different central nervous system (CNS) functions such as: regulation of angiogenesis and formation of the blood-brain barrier (BBB) during CNS development, control of vascular stability and angioarchitecture, regulation of capillary blood flow and clearance of toxic cellular byproducts. Interestingly, pericyte injury and/or degeneration are found in multiple neurological disorders exhibiting neurovascular dysfunction and BBB breakdown. This includes Alzheimer's disease (AD), dementia, stroke, CADASIL (cerebral autosomal dominant arteriopathy with subcortical infarcts) and amyotrophic lateral sclerosis. However, the exact role of pericyte dysfunction and loss in the pathogenesis of these disorders remains at present unclear.

Studies in pericyte-deficient mouse models have been carried out almost exclusively in transgenic animals with embryonically disrupted angiogenic signaling between endothelial-derived platelet-derived growth factor BB (PDGF-BB) and platelet-derived growth factor receptor β (PDGFRβ) in pericytes. Both, Pdgfb and Pdgfrβ null mice are embryonic lethal, and develop complete loss of pericytes resulting in BBB breakdown and diffuse microhemorrhages throughout the CNS. In contrast, mice with partially disrupted PDGF-BB and/or PDGFRβ signaling develop a moderate pericyte loss after birth that progresses with age leading to BBB breakdown with accumulation of blood-derived neurotoxic products in the CNS, and cerebral blood flow (CBF) reductions with ischemic and hypoxic changes. This slowly evolving vascular and BBB phenotype has been suggested to drive later in life an age-dependent, moderate neuron loss that becomes detectable at 6-8 months of age, or later, as shown in different Pdgfrβ-deficient models, or brain calcification, which is detectable in 1 year old Pdgfb-deficient mice, and progresses gradually with age.

Albeit extremely useful for understanding pericyte biology and providing important initial insights into their role in regulating neurovascular functions, models of PDGF-BB and PDGFRβ deficiency are not pericyte specific. Therefore, they cannot isolate the potential contribution of other PDGFRβ-expressing CNS cell types, or the developmental impact of embryonic loss of PDGFRβ signaling on neurovascular and possibly neuronal phenotype that develops later in adult life and aging brain. For instance, in addition to pericytes, vascular smooth muscle cells (VSMCs) express also PDGFRβ, and some studies suggest that even cultured neurons and embryonic neurons express PDGFRβ, although not confirmed in the embryonic CNS or adult brain by others.

It has become clear that in order to address the role of pericytes in the adult brain and disease, and to better understand their functions at the cellular and/or molecular level, the Inventors need to develop new inducible pericyte-specific models that can be used to turn on and off genes only in pericytes, but not other CNS cell types. An obvious first step towards this goal is to generate a pericyte-specific Cre line. This has been challenging, mainly because pericyte-specific genes have not been yet identified. Several pericyte markers, including PDGFRβ, the transmembrane chondroitin sulfate proteoglycan—neuron-glial antigen 2 (NG2), desmin, and many others are not unique to pericytes, and are shared with other brain cell types—most commonly VSMCs that are closely related to pericytes.

Therefore, to generate pericyte-specific Cre line the Inventors decided to use a double promoter strategy with both Pdgfrβ and Cspg4 promoters. The rationale for using Pdgfrβ promoter was that Pdgfrβ gene is normally expressed in mural cells of brain microvessels in the mouse and human CNS including pericytes on brain capillaries and VSMCs on arterioles and small arteries. Because PDGFRβ expression is enriched in pericytes relative to VSMCs, the Inventors anticipated that Pdgfrβ promoter will direct Cre expression preferentially to pericytes. The second promoter, Cspg4 gene encoding NG2 protein is expressed mainly in pericytes and oligodendrocyte progenitor cells. Cspg4 mRNA is also found in VSMCs, but the NG2 transmembrane protein is typically has relatively low expression in VSMCs, in contrast to its abundant expression in pericytes. The Inventors hypothesized that combining the two promoters of two different genes encoding proteins that are enriched in pericytes relative to other CNS cell types would give us a reasonable chance to generate pericyte-specific Cre mice. As the Inventors succeeded in generating pericyte-specific Cre line using this approach, the Inventors next crossed pericyte-specific Cre mice with the iDTR (Rosa26-LSL-DTR) mice that carries Cre-dependent human diphtheria toxin receptor (DTR). The Inventors then successfully ablated pericytes from the adult mouse brain after systemic administration of diphtheria toxin (DT), and observed a sequence of rapidly developing pathological events. First, the Inventors saw the direct impact of pericyte loss on brain microcirculation including strongly dysregulated CBF responses and BBB breakdown immediately after pericyte ablation. This was followed by a rapid development of behavioral deficits and acute secondary neurodegenerative changes.

Described herein is a transgenic mouse including a first promoter operably linked to a first DNA sequence and a second promoter operably linked to a second DNA sequence. In various embodiments, the first promoter includes a pericyte promoter. In various embodiments, the second promoter includes a pericyte promoter. In various embodiments, the first promoter includes Pdgfrβ and the second promoter includes Cspg4. In various embodiments, the first DNA sequence encodes a protein capable of binding to the second DNA sequence. In various embodiments, the protein includes a recombinase. In various embodiments, the recombinase includes flippase. In various embodiments, the second DNA sequence includes flippase recognition target. In various embodiments, the second DNA sequence includes cre. In various embodiments, the second DNA sequence includes cre estrogen receptor. In various embodiments, the first promoter includes Pdgfrβ, the second promoter includes Cspg4, the first DNA sequence encodes flippase and the second DNA sequence encodes cre and/or cre estrogen receptor. In various embodiments, the transgenic mouse includes a fluorescent reporter. In various embodiments, the fluorescent reporter includes tdTomato. In various embodiments, the transgenic mouse includes diphtheria toxin receptor.

Further described herein is a method of cellular screening comprising providing a quantity of cells, transfecting one or more vectors comprising a first promoter operably linked to a first DNA sequence, a second promoter operably linked to a second DNA sequence, and a fluorescent reporter, wherein the first DNA sequence encodes a protein capable of binding to the second DNA sequence, thereby inducing expression of the fluorescent reporter for cellular screening. In various embodiments, the first and/or second promoter are each, or both specific for a cell type. In various embodiments, the cells are capable of further differentiation. In various embodiments, the first promoter includes Pdgfrβ, the second promoter includes Cspg4. In various embodiments, the first DNA sequence encodes flippase and the second DNA sequence encodes flippase recognition target, cre and/or cre estrogen receptor.

Example 1

Animals

Mice were housed in plastic cages on a 12 h light cycle with ad libitum access to water and a standard laboratory diet. All procedures were approved by the Institutional Animal Care and Use Committee at the University of Southern California with National Institutes of Health guidelines. All animals were included in the study. Animals of both sexes 2-3 month old were used in the experiments. All animals were randomized for their genotype information. All experiments were blinded; the operators responsible for the experimental procedures and data analysis were blinded and unaware of group allocation throughout the experiments.

Generation of Pericyte Specific Cre Mouse Line.

Figure 5B:
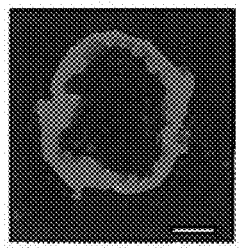
(FIG. 5B) The transmembrane chondroitin sulfate proteoglycan NG2 (red) encoded by Cspg4 gene does not show a detectable expression in PDGFRβ-positive (green) and smooth muscle actin (SMA, blue)-positive vascular smooth muscle cells (VSMCs) (teal color—colocalization of PDGFRβ and SMA) in the cortex of 3 month old C57BL/6 mice. Note, no colocalization of PDGFRβ and NG2. Bars=25 µm.
Figure 5C:
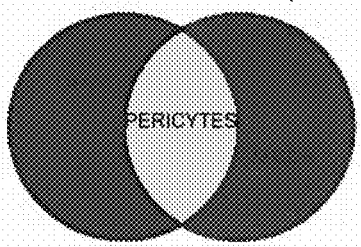
(FIG. 5C) Venn diagram depicting NG2⁺ and/or PDGFRβ⁺ positive cell populations in the adult CNS. The inner section (yellow) shows that pericytes are enriched in both PDGFRβ and NG2 compared to VSMC and oliogodendrocytes progenitor cells (OPCs) that do not express PDGFRβ.
Figure 5D:
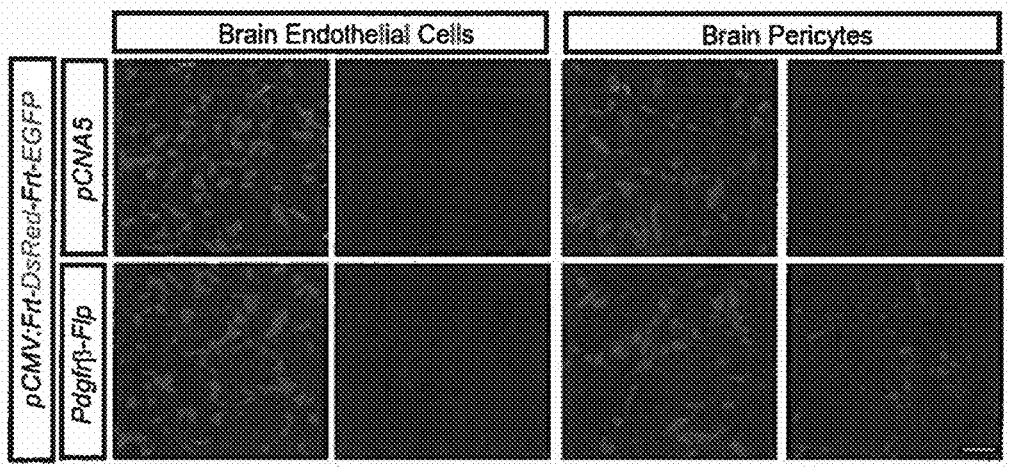
(FIG. 5D) Cultured murine brain endothelial cells and pericytes co-transfected with Pdgfrβ-Flp and a FLP-dependent GFP reporter construct (pCMV:Frt-DsRed-Frt-EGFP), showing EGFP expression only in pericytes, but not in endothelial cells. (E) Cultured primary murine endothelial cells and pericytes, showing that pericytes when co-transfected with Cspg4-FSF-CreER, Pdgfrβ-Flp and a Cre-dependent GFP reporter (pCALNL-GFP) successfully expressed GFP, but not endothelial cells.

A double promoter approach was utilized to achieve pericyte specific expression of Cre recombinase (FIG. 1A). More specifically, the Inventors generated two constructs: first, a Pdgfrβ-Flp construct that expresses Flippase recombinase (Flp) under the control of the Pdgfrβ promoter and second, a Cspg4-FSF-CreER construct that carries a Frt-Stop-Frt-CreER cassette under the control of Cspg4 promoter, using a BAC construct carrying the whole mouse Cspg4 gene and a targeting construct (provided by Dr. Nishiyama at the University of Connecticut) following a standard bacterial recombineering protocol. The Inventors tested both constructs in cultured primary murine pericytes and showed that pericytes co-transfected with Cspg4-FSF-CreER, Pdgfrβ-Flp and a reporter successfully expressed GFP, but not endothelial cells (FIG. 5D, E) or vascular smooth muscle cells (not shown). The constructs linearized with restriction endonucleases and purified with CsCl gradient method, were co-injected into C57BL/6 blastocysts via pronuclear injection at the Transgenic/Knockout Rodent Core at University of Southern California. Three litters of 25 pups were born; 5 of them were identified carrying both Pdgfrβ-flp cassette and Cspg4-FSF-CreER cassette. One founder line (Pdgfrβ-Flp; Cspg4-FSF-CreER) was established and verified by PCR, Southern blotting, and western blotting in brain microvessels showing Flippase expression, but not capillary-depleted brain (data not shown). The Pdgfrβ-Flp; Cspg4-FSF-CreER line was further characterized by crossing to Ai14 reporter line with floxed tdTomato (Jackson Laboratory, stoke #007908,). Administration of 40 mg/kg per day of Tamoxifen for seven consecutive days (Sigma T 5648) released the expression of tdTomato, specifically in pericytes, but not in other brain cell types including endothelial cells, smooth muscle cells, neurons, astrocytes and oligodendrocytes (FIG. 6).

Example 2

Diphtheria Toxin Dependent Ablation of Pericyte

Two-to-three month old Pericyte-Cre; iDTR or Pericyte-Cre; iDTR; Ai14 animals, two weeks after the end of tamoxifen injections, were administrated with intraperitoneal (i.p.) injection of 1 μg of DT/per day or vehicle for 10 consecutive days. Animals were sacrificed at 3 days post DT or vehicle treatment (FIG. 3A) or 15 days post DT or vehicle treatment (FIG. 4A) as indicated, and brains were collected and analyzed.

Example 3

Immunohistochemistry

Animals were anesthetized with an i.p. injection of 100 mg/kg of ketamine and 50 mg/kg of 10 xylazine, and transcardially perfused first with 15 ml saline, followed by 20 ml of 4% paraformaldehyde (PFA) in PBS. Brains were removed, and post-fixed overnight at 4° C. before brain sections were cut at 30 μm thickness. Sections were blocked with 5% normal donkey serum (Vector Laboratories)/0.1% Triton-X/0.01M PBS and incubated with primary antibody diluted in blocking solution overnight at 4° C. For detailed list of primary and secondary antibodies used to characterize pericytes, fibrin/fibrinogen deposits, axons, oligodendrocytes, neurons, astrocytes, microglia and VSMCs see Table below. To visualize brain microvessels, sections were incubated with Dylight 488-conjugated L. esculentum Lectin as the Inventors have previously reported. After incubation with primary antibodies, sections were washed in PBS and incubated with fluorophore-conjugated secondary antibodies as indicated in Table below, and then mounted onto slides with fluorescence mounting medium (Dako). Sections were imaged with a Zeiss LSM 510 confocal laser-scanning microscope using a series of high-resolution optical sections (1,024×1,024-pixel format) that were captured with a 25× water-immersion objective, with 1× zoom at 1-μm step intervals for Z-stacks. Laser settings for gain, digital offset and laser intensity were kept standardized between different treatments and experiments. Z-stack projections and pseudo-coloring were performed using ZEN software (Carl Zeiss Microimaging), and image post-analysis were performed using ImageJ software.

Example 4

Lasers and Band Pass (bp) Filters

The Inventors used a 488 nm argon laser to excite Alexa Fluor and Dylight 488, and the emission was collected through a 500-550 nm bp filter; a 543 HeNe laser to excite Alexa Fluor 568 and Cy3 the emission was collected through a 560-615 nm bp filter; a 633 HeNe laser to excite Alexa fluor 649 and the emission was collected through a 650-700 nm bp filter.

TABLE 1

| Antibodies Used in Studies | |
|---|---|
| Primary Antibodies | Secondary Antibodies |
| Pericyte Marker | |
| Goat anti-mouse aminopeptidase N/ANPEP (CD13; R&D systems, AF2335; 1:100) | Alexa fluor 488- or 568-conjugated donkey anti-goat (Invitrogen, A-11055 or A-11057; 1:500) |

TABLE 1-continued

Antibodies Used in Studies

| Primary Antibodies | Secondary Antibodies |
|---|---|
| Rabbit monoclonal anti-mouse PDGFRβ (Cat. No. 3169S, Cell Signaling; 1:200) | Alexa fluor 568-conjugated donkey anti-rabbit (Invitrogen, A-10042; 1:500) |
| Fibrinogen/Fibrin | |
| Rabbit anti-human fibrinogen (Dako, A0080; 1:500) | Alexa fluor 568-conjugated donkey anti-rabbit (Invitrogen, A-10042; 1:500) |
| Axons | |
| Mouse anti-mouse axonal SMI-312 neurofilament marker (SMI-312; BioLegend, SMI312; 1:500) | Alexa fluor 568-conjugated donkey anti-mouse (Invitrogen, A-10037; 1:500) |
| Oligodendrocytes | |
| Rabbit anti-mouse Olig2 (Millipore, AB9610; 1:200) | Alexa fluor 488- or 568-conjugated donkey anti-rabbit (Invitrogen, A-21206 or A-10042; 1:500) |
| Rabbit anti-mouse NG2 (Millipore, AB5320; 1:250) | Alexa fluor 488- or 568-conjugated donkey anti-mouse (Invitrogen, A-21202 or A-10037; 1:500) |
| Neurons | |
| Rabbit anti-mouse NeuN (Millipore, ABN78; 1:500) | Alexa fluor 568- or 647-conjugated donkey anti-rabbit (Invitrogen, A-10042 or A-31573; 1:500) |
| Vasculature | |
| Dylight 488-conjugated *L. esculentum* Lectin (Vector Labs, DL-1174; 1:200) | N/A |
| Microglia | |
| Rabbit anti-mouse ionized calcium binding adaptor molecule 1 (Iba-1; Wako, 019-19741; 1:1000) | Alexa fluor 488-conjugated donkey anti-rabbit (Invitrogen, A-21206; 1:500) |
| Astrocytes | |
| Rabbit anti-human Glial Fibrillary Acidic Protein (GFAP; Dako, z0334; 1:500) that cross react with mouse GFAP | Alexa fluor 647-conjugated donkey anti-rabbit (Invitrogen, A-31573; 1:500) |
| Vascular Smooth Muscle Cells | |
| Mouse monoclonal anti-mouse α-Smooth Muscle Actin - Cy3 (SMA; Sigma, C6198; 1:500) | N/A |
| Tight junctions | |
| Mouse monoclonal anti-human ZO-1 (Invitrogen, ZO1-1A12; 1:100)) that cross react with mouse ZO-1 | Alexa fluor 488- or 568-conjugated donkey anti-mouse (Invitrogen, A-21202 or A-10037; 1:500) |

Example 5

In Situ Fluorescent TUNEL Staining

Tissue was incubated for 30 min in 20 μg/ml Proteinase K and the In Situ Cell Death Detection Kit (Roche) was used per the manufacturer's instructions. Sections were coverslipped as described above. For each image, ten microns maximum projection z-stacks were reconstructed and analyzed using ImageJ. For quantification, TUNEL-positive cells that also demonstrated tdTomato-positive pericyte staining were quantified by using the Image J Cell Counter analysis tool. In each animal 5 randomly selected fields from the cortex were analyzed in 3 nonadjacent sections (~100 μm apart). Three animals per group were analyzed.

Example 6

Quantification

Pericyte Coverage and Numbers.
The quantitative analysis of pericyte coverage and numbers was restricted to CD13-positive cells that were associated with brain capillaries defined as microvessels ≤6 μm in diameter, as previously described. The endothelial-specific Lycopersicon esculentum lectin was used to visualize endothelial vascular profiles, and CD13 coverage of brain capillaries was determined as CD13-positive area (percentage) occupying lectin-positive endothelial capillary profiles, as previously. For each image, ten microns maximum projection z-stacks were reconstructed and analyzed using ImageJ. Pericyte numbers were determined by counting the number of CD13-positive cell bodies on the abluminal side of the endothelial membrane (lectin) that co-localized with DAPI (4',6-diamidino-2-phenylindole)-positive nuclei and tdTomato-positive cell bodies using the Image J Cell Counter plug-in, as the Inventors and others previously described. The number of pericytes was expressed per $mm^2$ of tissue.

Extravascular Leakages.

For each image, ten microns maximum projection z-stacks were reconstructed and analyzed using ImageJ. The levels of extravascular blood-derived fibrin and IgG deposits indicating BBB breakdown were determined as previously described.

NeuN-Positive Neuronal Numbers.

For each image, ten microns maximum projection z-stacks were reconstructed and analyzed using ImageJ. NeuN-positive neurons were determined using the ImageJ Cell Counter analysis tool. In each animal, five randomly selected fields from the cortex and the hippocampus in three nonadjacent sections (~100 µm apart) were analyzed. Six animals per group were analyzed.

Microglial Numbers.

For each image, ten microns maximum projection z-stacks were reconstructed and analyzed using ImageJ. In each animal, five randomly selected fields from the cortex in three nonadjacent sections (~100 µm apart) were analyzed for the number of Iba1-positive microglia. The number of microglia was determined using the ImageJ Cell Counter analysis tool. Three animals per group were analyzed.

GFAP-Positive Astrocyte Numbers.

For each image, ten microns maximum projection z-stacks were reconstructed and analyzed using ImageJ. GFAP-positive astrocytes that also demonstrated DAPI-positive nuclear staining were quantified by using the Image J Cell Counter analysis tool. In each animal five randomly selected fields from the cortex were analyzed in three nonadjacent sections (~100 µm apart). Three animals per group were analyzed.

Immunofluorescent ZO-1 Tight Junction Length.

For each image, ten microns maximum projection z-stacks were reconstructed and analyzed using ImageJ. The length of ZO-1-positive tight junctions occupying lectin-positive capillary profiles was determined using the NeuronJ plugin for ImageJ, expressed as the length of ZO-1 (mm) over the lectin-positive capillary area ($mm^2$) as the Inventors have previously reported. ZO-1 and lectin stainings were performed as described above. The length of ZO1-positive tight junctions was normalized to the total area of lectin-positive microvessels using the Image J Area measurement tool.

Example 7

Isolation of Brain Microvessels and Cell Cultures

Brain microvessels were isolated using dextran gradient centrifugation followed by sequential cell-strainer filtrations, as the Inventors have previously described. Briefly, cerebral cortices devoid of cerebella, white matter, and leptomeninges were prepared and cut into small pieces in ice-cold PBS containing 2% fetal bovine serum (FBS), then homogenized by Dounce tissue grinder (0.25 mm clearance) with five strokes. Dextran (70 kDa, Sigma) was subsequently added to yield a final concentration of 16% and the samples were thoroughly mixed. The samples were then centrifuged at 6,000 g for 15 min. The microvessel-depleted brain (brain tissue minus capillaries) remained on top of the dextran gradient and was collected. The capillary pellet located at the bottom of the tubes was collected and sequentially filtered through a 100 µm and 45 µm cell strainer (BD Falcon). The capillaries remaining on top of the 45 µm cell strainer were collected in PBS and either lysed for immunoblotting analysis, cytospun for fluorescent staining analysis, or processed for establishing primary pericyte cell cultures as described below.

Brain Pericyte Culture

Primary mouse brain pericytes were isolated for in vitro cultures as the Inventors previously described. Briefly, isolated microvessel fragments were digested for 12 h at 37° C. with collagenase A (Roche, 10103586001), constant shaking and vigorous pipetting every 3-4 h. The cells were then spun down and washed with PBS and then plated in a complete medium containing DMEM, 10% FBS, 1% non-essential amino acids, 1% vitamins and 1% antibiotic/antimycotic on plastic (non-coated) tissue culture plates. After 6 to 12 h the non-adherent cells were rinsed away and fresh medium was replaced every 2-3 days. Cultures were confirmed to be morphological consistent with pericyte cultures and PDGFRβ-positive, CD13-positive, NG2-positive, GFAP-negative, AQP4-negative, MAP2-negative, NeuN-negative, VWF-negative, and Iba1-negative, as the Inventors previously reported.

Brain Endothelial Culture

Primary mouse brain endothelial cells were isolated and cultured as previously described. Briefly, isolated brain microvessels were resuspended in 9 ml DMEM and add 1 ml collagenase/dispase (final concentration is 1 mg/ml) and 0.1 ml DNAse I (1 mg/ml in PBS), and digested the solution for 1 hr at 37° C. on an orbital shaker at 180 rpm. The cells were centrifuged at 1,000×g for 12 min, the pellet were resuspended in 10 ml of complete culture medium (Cell Biologics, Cat. #: M1168; containing 5% FBS, 1% non-essential amino acids, 1% vitamins and supplemented with ECGS endothelial cell growth supplement, VEGF, heparin and EGF), plated in a T25 tissue culture flask pre-coated with collagen IV (0.4 mg/ml) and 100 µl fibronectin (0.1 mg/ml), and cultured at 37° C. with 5% $CO_2$ in a humidified incubator. After 6 to 12 h the non-adherent cells were rinsed away and fresh medium was replaced every 2-3 days until the cell population is confluent. Cultures were confirmed to be morphological consistent with primary endothelial cultures with cobble stone like shape and von Willebrand factor-positive, CD31-positive, VE-cadherin-positive, PDGFRβ-negative, CD13-negative, α-Smooth Muscle Actin-negative, NG2-negative, GFAP-negative, AQP4-negative, MAP2-negative, NeuN-negative, Iba1-negative, as the Inventors previously reported.

Brain VSMC Culture

Primary mouse brain vascular smooth muscle cells were isolated and cultured as previously described. Briefly, isolated brain microvessels were resuspended in 500 µl complete culture medium (Cell Biologics, Cat. #: M2268-Kit; containing 10% FBS, 1% non-essential amino acids, 1% vitamins and supplemented with insulin, EGF and FGF) with 0.05% collagenases/dispase and incubated for 2.5-3 h in a 37° C. water bath. An equal volume of ice-cold complete culture medium supplemented with 5 mM EDTA was then added. The cells were centrifuged at 1,000×g for 12 min, the pellet were resuspended in 10 ml of complete culture medium, plated in a T25 tissue culture flask and cultured at 37° C. with 5% $CO_2$ in a humidified incubator. After 6 to 12 h the non-adherent cells were rinsed away and fresh medium was replaced every 2-3 days until the cell population is confluent. Cultures were confirmed to be morphologically consistent with VSMC cultures and α-Smooth Muscle Actin-positive, calponin-positive, SM22α-positive, von Willebrand factor-negative, GFAP-negative, AQP4-negative, MAP2-negative, NeuN-negative, Iba1-negative, prolyl-4-hydroxylase-negative, as the Inventors previously reported.

Example 8

Western Blots

Brain microvessels and capillary-depleted brains were lysed in RIPA buffer (50 mM Tris, pH 8.0, 150 mM NaCl, 0.1% SDS, 1.0% NP-40, 0.5% sodium deoxycholate and Roche protease inhibitor cocktail). Samples were then subjected to SDS-Page gel electrophoresis and transferred to a nitrocellulose membrane. Membranes were blocked with 5% milk, incubated with primary antibody, and then incubated with the appropriate HRP-conjugated secondary antibody. Membranes were then treated with Immobilon Western ECL detection buffers (Millipore), exposed to CL-XPosure film (Thermo Scientific) and developed in a X-OMAT 3000 RA film processor (Kodak). Primary antibodies used for western blotting are rabbit monoclonal anti-mouse PDGFRβ (Cat. No. 3169S, Cell Signaling), goat polyclonal anti-mouse CD31 (Cat. No. AF3628, R&D Systems), mouse monoclonal anti-human DTR (Cat. No. 71-501, BioAcademia), and rabbit monoclonal anti-human β-actin that cross-react with mouse β-actin (Cat. No. 4970S, Cell Signaling).

Example 9

Cranial Window

Animals were initially anesthetized with 100 mg/kg of ketamine and 50 mg/kg of xylazine and were placed on a heating pad (37° C.). The cranium of the mouse was firmly secured in a stereotaxic frame. A high speed dental drill (tip FST 19007-05, Fine Science Tools Inc., Foster City, Calif.) was used to thin a square cranial window about 2×2 mm over the parietal cortex, and 45 degree forceps were used to remove the square piece of skull. Gelfoam (Pharmacia & Upjohn Company, Kalamazoo, Mass.) was applied immediately to control any cranial or dural bleeding. A sterile 5 mm glass cover slip was then placed on the dura mater and sealed with a 1:1 mixture of bone cement and cyanoacrylate based glue.

Example 10

Laser-Doppler Flowmetry (LDF)

CBF responses to hindlimb stimulation in anesthetized mice (~1% isoflurane) were determined using laser-Doppler flowmetry as previously described. The tip of the laser-Doppler probe (Transonic Systems Inc., Ithaca, N.Y.) was stereotaxically placed 0.5 mm above the cranial window over the hindlimb region of the primary somatosensory cortical area. CBF was recorded following electrical stimulation of the hind-limb using a 60 s long stimulus (7 Hz, 2 ms pulse duration). The percentage increase in CBF due to stimulation was obtained by subtracting the baseline CBF from the stable maximum plateau value reached during stimulus, and averaged over three trials per mouse. For CBF response to drug application, the LDF probe was placed stereotaxically over the center of an open cranial window (center at AP=−0.94 mm, L=1.5 mm). Drugs (10 μM Acetylcholine, and 400 μM Adenosine, all from Sigma) were superfused individually over the window, and responses recorded, as the Inventors reported previously. Arterial blood pressure was monitored continuously during the experiment. pH and blood gases were monitored before and after CBF recordings.

Example 11

Behavioral Tests

Novel Object Location

Novel object location test was performed as the Inventors have previously reported. Animals were placed in a 30 cm³ box and allowed to habituate to the testing area for 10 min. Animals were then placed back in their cages and 2 identical approximately 5×5 cm objects were placed in the top left and right corner of the testing area. Animals were allowed to explore the two objects in the testing area for 5 min before being returned to their cages. After an hour interval one of the objects was relocated and the animals were allowed to explore the testing area once again for 3 min. After each trial, the testing area and the objects were thoroughly cleaned with 70% ethanol solution. All the trials, including habituation, were recorded with a high resolution camera and the amount of time each animal spent exploring the objects was analyzed. Any animals that presented a preference for either of the two identical objects, before replacement with the novel location, were eliminated from the analysis. Both male and female animals were used in the study. Four time points were used in the Inventors study as indicated in the FIG. 4 legend.

Contextual Fear Conditioning

Long-term memory formation paradigm in contextual fear conditioning was adapted from a previously described protocol with modifications. The experiment was performed using conditioning chamber made of plexiglas housed in a soundproof isolation cubicle and equipped with a stainless-steel grid floor connected to a solid-state shock scrambler. The scrambler was connected to an electronic constant-current shock source that was controlled via an interface connected to a computer running FreezeFrame software (Coulbourn Instruments, Allentown, Pa., USA). A digital camera was mounted on the steel ceiling and behavior was recorded. During training, mice were placed in the conditioning chamber for 5 min and received four footshocks (0.25 mA, 1 sec) at 1-min interval starting 2 min after placing the mouse in the chamber. Contextual long-term memory was tested in the same chamber the next day without footshock applied. Hippocampus-dependent fear memory formation was evaluated by scoring freezing behavior (the absence of all movement except for respiration). Percentage of total freezing time was assessed using the automated FreezeFrame system with a threshold set at 10%. Both male and female animals were used in the study.

Example 12

Statistical Analysis

Sample sizes were calculated using nQUERY assuming a two-sided alpha-level of 0.05, 80% power, and homogeneous variances for the 2 samples to be compared, with the means and common standard deviation for different parameters predicted from published data and the Inventors previous studies. Data are presented as mean±s.d., or means±s.e.m. as indicated in the figure legends. For comparison between two groups, F test was conducted to determine the similarity in the variances between the groups that are statistically compared, and statistical significance was analyzed by Student's t-test. For multiple comparisons, Bartlett's test for equal variances was used to determine the variances between the multiple groups and one-way analysis of variance (ANOVA) followed by Bonferroni's post hoc test was used to test statistical significance, using GraphPad Prism software. A P value of less than 0.05 was considered statistically significant.

Example 13

Generation and Characterization of an Inducible Pericyte-Specific Cre Mouse Line In order to develop new transgenic models to study the role of pericytes in the CNS, the Inventors generated pericyte-specific Cre driver mouse line using double promoter strategy with the murine Pdgfrβ and Cspg4 promoters. The Inventors decided to use a double promoter approach rather than a single promoter because no pericyte-specific gene has been identified to date. Pdgfrβ expression is enriched in pericytes compared to VSMCs, whereas Cspg4 gene encoding NG2 is expressed in pericytes and oligodendrocyte progenitor cells. The NG2 protein levels in PDGFRβ-positive VSMCs in the adult mouse CNS are typically low or barely detectable (FIG. 5A-C) in contrast to abundant NG2 expression in pericytes. The Inventors reasoned that combining the two promoters that drive expression of genes whose products are both enriched in pericytes relative to other CNS cell types would increase the Inventors chance to generate pericyte-specific Cre mice.

Figure 5E:
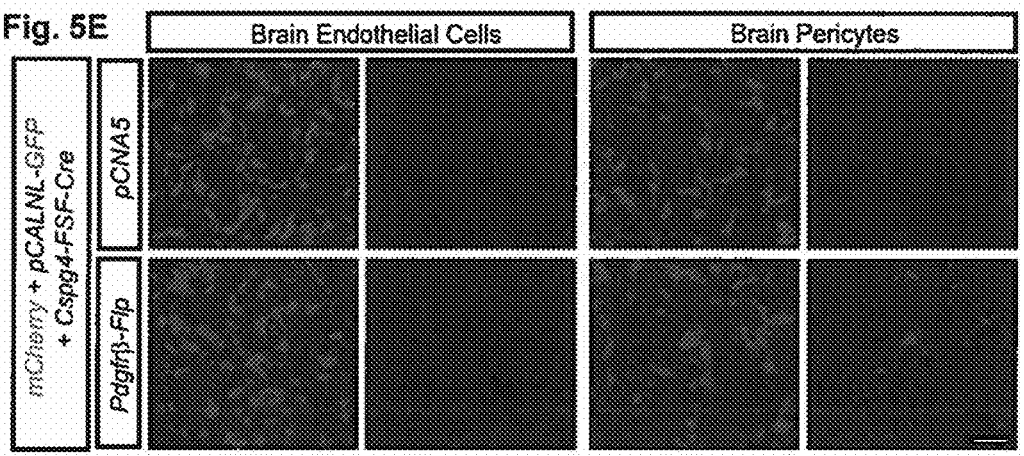

First, the Inventors made two transgenic constructs: one expressing Flippase recombinase (Flp) under the control of the Pdgfrβ promoter (SEQ ID NO:1), and the other carrying an Frt-Stop-Frt-CreER cassette (Frt: flippase recognition target; CreER: recombinant protein between Cre recombinase and a mutated ligand binding domain of the estrogen receptor under the control of Cspg4 promoter (SEQ ID NO:2) (FIG. 1A left). Using these two promoters, the Inventors hypothesized that tamoxifen (TAM)-inducible CreER expression will be released via Flippase only when both promoters are active in the same cell. The Inventors tested initially the Inventors hypothesis and cell specificity of the two-promoter strategy using in vitro primary cell cultures of mouse brain pericytes, endothelial cells and VSMCs in combination with Cre-dependent reporters. The Inventors found that after co-transfection with Cspg4-FSF-CreER, Pdgfrβ-Flp and a Cre-dependent green fluorescent protein (GFP) reporter (pCALNL-GFP) the only cell type that allowed for both Flp and CreER expression resulting in GFP expression were pericytes (FIG. 5D-E), In contrast, primary brain endothelial cells (FIG. 5D-E) and VSMCs (not shown; see supplementary methods) failed to turn on successfully Cre-dependent GFP expression.

Figure 6A:
(FIG. 6A) Representative confocal images, showing restricted tdTomato expression in PDGFRβ⁺ pericytes. Bar=20 µm.
Figure 6B:
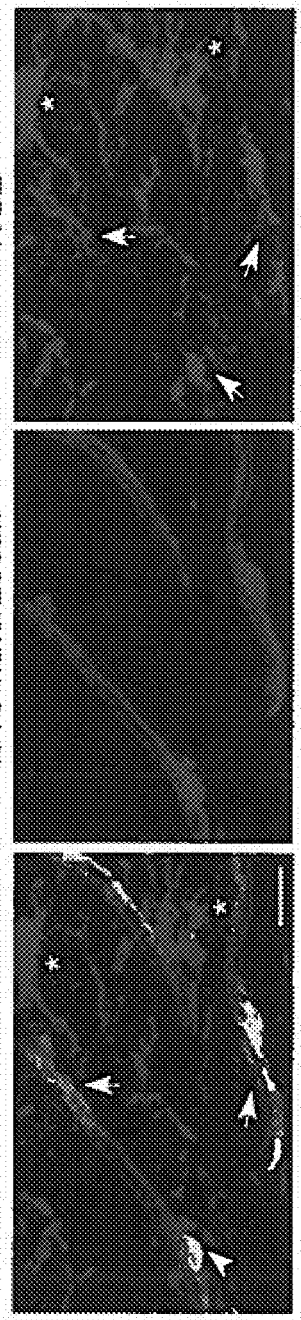
(FIG. 6B) Representative confocal images, showing expression of tdTomato in NG2⁺ pericytes (Arrows), but not NG2⁺ polydendrocytes (Stars). Bar=20 µm.
Figure 6C:
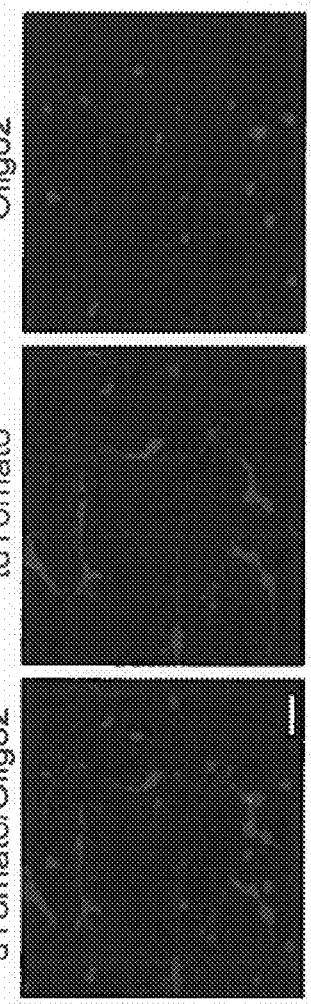
(FIG. 6C) Representative confocal images showing that tdTomato is not expressed in Olig2⁺ oligodendrocytes. Bar=20 µm.

To test the Inventors hypothesis in vivo, the Inventors generated Pdgfrβ-Flp; Cspg4-FSF-CreER mice by co-injecting both linearized constructs in C57BL/6 blastocysts, as previously reported. One founder line that stably carried both Pdgfrβ-Flp cassette and Cspg4-FSF-CreER cassettes as shown by PCR and Southern blotting analysis, and western blotting analysis of brain microvessels confirming Flippase expression (see supplementary methods), was selected for further characterization. To characterize Cre expression pattern, the Inventors crossed Pdgfrβ-Flp; Cspg4-FSF-CreER mice with the Ai14 tdTomato reporter line generated with SEQ ID NO:3 (FIG. 1A right). The expression of tdTomato reporter was induced with TAM. After TAM treatment, the Inventors found that tdTomato was expressed only in the mural cells of brain capillaries (<6 μm), but was completely absent from mural cells of small arterioles containing smooth muscle actin (SMA)-labeled VSMCs (FIG. 1B-D). Triple-labeling with a pericyte marker CD13 and an endothelial marker CD31 confirmed that tdTomato expression colocalized exclusively with CD13-positive pericytes, and was not found in CD31-labeled endothelial cells (FIG. 1E). Furthermore, using other pericyte markers, such as PDGFRβ and NG2, the Inventors confirmed that tdTomato expression is restricted only to PDGFRβ-positive and NG2-positive pericytes (FIG. 6A, B). No any other brain cell types expressed tdTomato including: NG2-positive polygodendrocytes (FIG. 6B), Olig2-positive oligodendrocytes (FIG. 6C), glial fibrillar acidic protein (GFAP)-positive astrocytes (FIG. 6D-E), NeuN-positive neurons (FIG. 6F) or Ionized calcium binding adaptor molecule 1 (Iba1)-positive resident microglia (FIG. 6G).

After validating the specificity of Cre expression in pericytes, the Inventors next determined the induction efficiency of tdTomato in Pdgfrβ-Flp; Cspg4-FSF-CreER mice using different TAM injection protocols. This experiment showed that tdTomato expression was dependent on TAM dosage, with 24% 42% and 71% of pericytes expressing dtTomatio after 2, 4 and 7 TAM injections, respectively, as determined by double positive tdTomato$^+$ and CD13$^+$ cells, respectively (FIG. 1F-G). Collectively, the Inventors findings suggest that a Pdgfrβ-Flp; Cspg4-FSF-CreER mouse is an inducible novel pericyte-specific Cre mouse line.

Inducible pericyte ablation in the Pericyte-CreER; iDTR mouse To achieve specific ablation of the pericyte lineage from the mouse brain the Inventors crossed the Inventors Pericyte-CreER mice (FIG. 1) with an iDTR line that carries Cre-dependent human diphtheria toxin receptor (DTR) that leads to cell death after administration of a low dose of diphtheria toxin (DT) (FIG. 2A, also see supplementary methods). DT crosses the blood-brain barrier, and one molecule of its subunit A is sufficient to cease protein synthesis in DTR-expressing cells causing cell death. Here, the Inventors first show by immunblotting that DTR is indeed expressed in brain microvessels isolated from Pericyte-CreER; iDTR mice treated with TAM (7 injections, 40 mg/kg i.p.) but not vehicle (FIG. 2B-C). In contrast, DTR levels were undetectable by immunblotting of capillary-depleted brain homogenates (not shown). For robust depletion of DTR-expressing cells, yet without introducing any non-specific toxicity to the animals, the Inventors used a DT administration protocol as developed previously to successfully ablate DTR-expressing microglia from the brain. Two weeks after TAM, DT (1 μg i.p. per day for 10 consecutive days) compared to vehicle lead to a 90% loss in DTR protein levels in brain capillaries of Pericyte-CreER; iDTR mice, as shown 3 days after DT or vehicle treatment (FIG. 2B-C). Loss of DTR receptor reflecting loss of DTR-expressing cells was associated with a 60% loss of PDGFRβ protein, a marker of brain capillary pericytes (FIG. 2B-C), but not CD31, a marker of brain capillary endothelial cells. Collectively, these data suggest preliminarily that DT is killing likely PDGFRβ-positive pericytes expressing DTR.

Tissue analysis from Pericyte-CreER; iDTR mice indicated a 95% loss of tdTomato-positive pericytes in brain capillaries (<6 μm in diameter) in the cortex and hippocampus 3 days after DT treatment compared to vehicle, as confirmed by double immunostaining with the pericyte marker CD13 (FIG. 2D-E). This efficiency of ablation was consistent with previous reports showing comparable DT-induced ablation of DTR-expressing microglia and oligodendrocytes using the same iDTR strain. In addition, no changes were observed in the number of astrocytes, astrocytic endfeet coverage on microvessels or microglia density 3 days after DT treatment (data not shown), indicating that DT and subsequent pericyte ablation did not induce acutely gliosis or neuroinflammatory response.

By quantifying the number of CD13-positive pericyte cell bodies, the Inventors found 60% and 58% reductions in pericyte density in the cortex and hippocampus, respectively, in 3 month-old TAM-treated pericyte-CreER; iDTR mice 3 days after DT treatment compared to vehicle (FIG. 2D, F). This finding is consistent with 60% loss of PDGFRβ protein levels shown by western blotting of brain microvessels of TAM-treated pericyte-CreER; iDTR mice after DT compared to vehicle (FIG. 2B-C). Pericyte cell death was next confirmed by showing that perivascular tdTomato-positive nuclei contained fragmented DNA in TAM-treated pericyte-CreER; iDTR mice 3 days after DT treatment compared to vehicle, as shown by terminal deoxynucleotidyl transferase dUTP nick end labeling (TUNEL) staining (FIG. 2G, H). Finally, CD13-positive pericyte coverage of cortical lectin-positive endothelial capillary profiles indicated a 50% reduction in perciyte capillary coverage in TAM-treated pericyte-CreER; iDTR mice 3 days after DT treatment compared to vehicle (FIG. 2I, J). Somewhat lower reduction in coverage compared to loss of pericyte cell bodies was consistent with previous reports suggesting that the remaining pericytes are able to moderately compensate for the loss of pericyte pool by overstretching their processes extended along the capillary wall. Importantly, TAM-treated control iDTR mice that received the same DT injection protocol showed no changes in pericyte coverage (FIG. 7A, B), indicating DT-induced pericyte ablation is specific for pericyte-CreER; iDTR mice.

Blood flow dysregulation and BBB breakdown after pericyte ablation Analysis of CBF changes in response to hind limb electrical stimulus (also see supplementary methods) measured by the laser Doppler flowmetry (LDF) in 3 month-old TAM-treated pericyte-CreER; iDTR mice revealed a 50% reduction in CBF response 3 days after DT treatment compared to vehicle (FIG. 3B). No significant change in CBF responses were observed in TAM and vehicle treated pericyte-CreER; iDTR mice (FIG. 3B), and/or in control iDTR animals that received TAM and DT treatment (FIG. 7C). These data suggest that DT treatment did not result in CBF changes in iDTR control mice consistent with findings showing that DT treatment does not lead to a loss of pericytes in iDTR control mice unless these mice are crossed with Pericyte-CreER mice. Reductions in CBF responses in 3 month-old TAM-treated pericyte-CreER; iDTR mice correlated positively with the decrease in pericyte coverage (FIG. 3C), demonstrating a strong relationship between pericyte loss and CBF dysregulation.

To rule out possible involvement of endothelial or VSMCs dysfunction in the observed CBF dysregulation in 3 month-old TAM-treated pericyte-CreER; iDTR mice, the Inventors next tested CBF responses in the presence of endothelium-dependent vasodilator acetylcholine for receptor-mediated vasodilation (FIG. 8A), and VSMC-dependent vasodilator adenosine (FIG. 8B). These experiments showed no difference in CBF response in the presence of either acetylcholine or adenosine 3 days after DT treatment or vehicle (FIG. 8A, B). These data rule out abnormal endothelial and VSMCs responses to a stimulus and indicate that the observed CBF dysregulation is primarily due to pericyte loss.

To investigate whether pericyte ablation impairs BBB integrity, the Inventors determined accumulation of plasma-derived proteins in the cortex of 3 month old pericyte-CreER; iDTR mice 3 days after DT or vehicle treatment. Immunostaining for plasma-derived immunoglobulin G (FIG. 3D) and fibrin (FIG. 3E) deposits demonstrated >4-fold increase in the cortex of 3 month-old TAM-treated pericyte-CreER; iDTR mice 3 days after DT treatment compared to vehicle (FIG. 3F). In contrast, control iDTR animals that received TAM and DT did not show any BBB changes, as expected (FIG. 9A-C).

As the paracellular transport of solutes across the BBB including transport of macromolecules is regulated by tight junction proteins, the Inventors next examined tight junction protein expression. Immunohistological analyses showed a 50% reduction in the ZO-1 length on brain capillaries in 3 month-old TAM-treated pericyte-CreER; iDTR mice 3 days after DT treatment compared to vehicle (FIG. 3G, H). No changes in ZO-1 expression were observed in iDTR control animals treated with TAM and DT (FIG. 9D-E). Pearson's correlation analysis revealed that the ZO-1 length within the brain capillary endothelium strongly correlated with the degree of pericyte coverage in 3 month-old TAM-treated pericyte-CreER; iDTR mice (FIG. 3I), whereas the degree of fibrin extravasation negatively correlated with the ZO-1 length in the same mice (FIG. 3J).

Taken together, the Inventors data indicate that blood flow dysregulation and BBB dysfunction occur immediately after acute ablation of brain pericytes. Behavioral deficits and acute neurodegeneration after pericyte ablation As CBF reductions and BBB breakdown can results in slow development of neurodegenerative changes, the Inventors next examined behavior and tissue neuronal changes in 3 month-old TAM-treated pericyte-CreER; iDTR mice before, during and after DT or vehicle treatment as shown in a schematic in FIG. 4A. Behavior tests of hippocampal function, including novel object location (FIG. 4B) and fear conditioning (FIG. 4C), in 3 month-old TAM-treated pericyte-CreER; iDTR mice treated with DT did not show deficits compared to vehicle before treatment (0 d), in the middle of DT treatment (6 d), and 3 days after the last DT injection (FIG. 4 B, C), a time point when vascular phenotype has been already established (FIG. 3). Interestingly, DT-treated mice developed significant behavior deficits 15 days after DT treatment (FIG. 4B-C), suggesting that functional dysfunction occurs rapidly after pericyte-dependent microvascular degenerative changes occur. Moreover, tissue analysis indicated a significant loss of neurons and reductions in neuritic density 15 days after DT treatment relative to vehicle. This has been shown by a 20-25% loss of NeuN-positive neuronal cell bodies (FIG. 4 D, F), and a 30-40% reduction in SMI-312-positive neuritic density (FIG. 4 E,G) in the somatosensory cortex and hippocampus, respectively, in 3 month-old TAM-treated pericyte-CreER; iDTR mice 15 days after DT treatment compared to vehicle (FIG. 4 D-G). No significant neuronal or neuritic changes were observed in these animals before DT treatment and 3 days after last DT injection compared to vehicle (FIG. 4 F, G). Control iDTR animals treated with TAM and DT showed no differences in novel object location and fear conditioning (FIG. 9F-G), and had normal neuron counts and neuritic density (FIG. 9H-J). Collectively, the Inventors data show that secondary neuronal degeneration and structural changes develop rapidly after neurovascular changes triggered by pericyte ablation.

Example 15

Pericyte Rescue Model

A previous report has demonstrated that replacement of PDGF-B through targeting the highly expressed ROSA26 allele in Pdgftbtet mice rescued the vascular phenotype. However, the influences in neuronal structure and function were not studied. In order to clearly delineate the role of pericytes in maintaining vascular and neuronal function, we have designed a conditional rescue model which combines a tetracycline controlled gene expression system with Cre-Loxp recombination system, in $Pdgf\beta^{+/-}$ or $Pdgftr^{fl/fl}$ directed models of pericyte deficiency. To achieve this goal we will create one novel transgenic mouse in which a Tet-on (tetO) response element immediately precedes a Loxp-stop-Loxp-Pdqfrβ cassette. This pTRE-LSL-Pdgfrβ mouse will then be crossed to cell type specific Cre lines to release the Stop cassette in front of Pdgfrβ (cell type specific TetO-Pdgfrβ). In the same time, $Pdgf\beta^{+/-}$ or $Pdgftr^{fl/fl}$ mouse will be crossed with commercially available mouse line which expresses the tetracycline transactivator protein (rtTA) using ROSA26 allele. After crossing these two new lines, the progeny carrying all the allelles (TetO Pdgfrb, rtTA and defected Pdgfrβ) will express functional PDGFRB protein in the presence of Doxycycline (supplemented in the drinking water). Importantly, expression of PDGFRβ can be quantitatively achieved with varying doses of Doxycycline and be reversible turned off following cessation. More specifically, the progeny will be crossed to Cspg4-Cre for pericyte specific complementation of PDGFRB, or SMMHC-cre 9(Myhll-Cre,-EGFP) to enable smooth muscle specific cornplernentation. Our hypothesis is: since pericyte loss in Pdgfβ$^{+/-}$ or Pdgftr$^{f7/f7}$ mouse is a result of PDGFR deficiency, supplement of certain amount of functional PDGFRβ in pericytes, but not in smooth muscle cells, potentially can reverse the phenotypes of pericyte loss, vascular and neuronal dysfunctions in adulthood. This novel pTRE-LSL-Pdgfr/3 mouse will give provides an opportunity of expressing PDGFR Pdgfβ$^{+/-}$ or Pdgftr$^{f7/f7}$ in a cell type specific and reversible manner to reveal the nature of pericytes in the aging brain. Currently, the pTRE-LSL-Pdgfrβ construct has been successfully generated and sequenced laboratory. When it is transfected into Tet-on 293T cells, no leaky expression of PDGFRβ was detected, and in the presence of Doxycycline (1, 10, 100, 1000 ng/ml), strong and dose-dependent expression of PDGFRI3 was successfully induced, indicating this construct is correct and tightly controlled. After linearization with Scal, purify and send for pronuclear injection into C57BL/6 blastocysts.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are sources of pericytes, vectors encoding pericyte specific promoter and/or genes, combinations of these elements, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law.

Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A transgenic mouse whose genome comprises:
   i) a nucleic acid sequence encoding flippase operably linked to a platelet-derived growth factor receptor B (PdgfrB) promoter; and
   ii) a nucleic acid sequence encoding a flippase recognition target-stop-flippase recognition target-recombinase cassette operably linked to a chondroitin sulfate proteoglycan 4 (Cspg4) promoter,
   wherein the transgenic mouse is capable of being crossed with a Cre-reporter mouse whose genome comprises: i) a nucleic acid sequence encoding a loxP-flanked-stop cassette; and (ii) a nucleic acid sequence encoding a reporter protein or diphtheria toxin receptor, wherein the cassette prevents transcription of the reporter protein or the diphtheria toxin receptor in the Cre-reporter mouse, such that the reporter protein or diphtheria toxin receptor is specifically expressed in pericytes of offspring obtained from the cross.

2. The transgenic mouse of claim 1, wherein the fluorescent reporter protein comprises tdTomato.

3. The transgenic mouse of claim 1, wherein the nucleic acid sequence encoding flippase operably linked to a platelet-derived growth factor receptor B (PdgfrB) promoter is SEQ ID NO: 1.

4. The transgenic mouse of claim 1, wherein the nucleic acid sequence encoding a flippase recognition target-stop-flippase recognition target-recombinase cassette operably linked to a chondroitin sulfate proteoglycan 4 (Cspg4) promoter is SEQ ID NO: 2.

* * * * *

SEQUENCE LISTING

```
<160> NUMBER OF SEQ ID NOS: 3

<210> SEQ ID NO 1
<211> LENGTH: 9208
<212> TYPE: DNA
<213> ORGANISM: Artificial Sequence
<220> FEATURE:
<223> OTHER INFORMATION: pCAG pdgfrbFlp

<400> SEQUENCE: 1
gtcgaccgtt gcttccttga tgtttgcttg tgagctctgg gaaggggcgt ggggaggcag      60
gtcacatagt aggtgttcag cgaactaact cccttcatgc agatgcacaa tgggagaaac     120
aggacagcct gaaattaggg gtgagaggcc ccacggaaga catattatgt gccttcagtc     180
aggttctgta cccacttctg ggtcttaaga gccagtgttc tcgtgaggga gaaacaatat     240
cgtcttcaag ggtgctactg ctgtatttct ttgagacttc tgtatatggt aggaggatgt     300
gccacagtgc cctgtgttcc gggggcactg aggtagcata ggatagggtg gttgggaggc     360
tggggtaagt atgaatggac atgtcttgaa cttcaaatgt cctgctttag tggagcctgg     420
cccgggaaga gggtttccaa gaatctctgt tgaagatgac tcatgtccct gctgcctcc      480 tcggacacgt gctccaagtg tcaacggtgc tgtgactcct accctaagac ttgactttcc     540
agctacaggt agagcagcta taggtagggt ctacctatct gctcacagtg agtagtaggg     600
aaggatgctg ggctaaatca tcctctaccg ctcaggcacc tccctgcaaa gccttccatt     660
tcctgagctt gtccagtaga cgaccctaga ggacgtcctt ccggacaccc aagctgactg     720
tgctaaggtc tgggacgtga gctgcttcct cacacccat gcctgctctg cgagcctcca     780
gggcagcttc aggagcgtgg gagagccagc tgtggtagct gctggtgctg agctgatcca     840
cagggacatc tcccatgggg atcccttcc gggcccctca gcccacactc cacagagccc     900
tgcttcctgc tctgacagtg agggaggtat cagggattat gcgcaacctg gacccctcct     960
ctagggcaga acgtgggtat aaaacttggg gccaagcctt tgttgccatg gtatctgtgc    1020
tcacactgca ggatcataca gcctcacatg agccactctg tcaagacccc ttacgttggc    1080
tataaagaga gtgggtggag gggggtcctt ccggccctga ttatggactc ctgtgacagc    1140
agccccaggg aggactggtt atcctttgta gttctcctct ccttctgcct ctaggctcgc    1200
cccaaacctg tatgaatctt gtactcatgt ccctcacagc atgtgaggtg ggcacacaag    1260
cctttatttt aaaaacccca aggctctggg cattttgaga gtcacacagc taagacgcaa    1320
ctgagttcgg agcctcaggc ttagcgctca gattctcatg catgaagtag accgccaatc    1380
tgcgtaggtg agaaaaaagc gtgacgcccc aaggcctgga gccccttctg aactctaccc    1440 accaccccgct ctcagcagct tttccctcag tgtttgacca taggtaaacc ggctcccagg    1500
atctgggcgt ggaatgagtg tgcttgattc gttctgtcca cagtggggct gggaccatgc    1560
tggccaccct agcgtgatgc tacatactcg ttcacccaca gactgctgaa gaagctgcgg    1620
gtgcagaccc ggccctgact tacctgctgt ctagagcaga aagcaggctg ggcagctcag    1680
```

```
ggacattcaa caaggtcttc cagcttcaaa cagagaggct ggagtcagaa ctcaacttta   1740
gtctctgggt ccaggccttc gagagtgccc tgtggcactc tgtgtagttt tgtatcgctt   1800
gcatcccatc acagggagga gaaacagctc ctgtgcccac caagggttaa tggtggtaga   1860
actaagtgct tccagatggg ccagcggatg gctgggctgg ccggaaatgg cagcccccc    1920 ccccaatctc tcgaggatcg gccaccgcca ctccttccct ctacgctgtg tctttggccc   1980
ccagctgtcc cctgccccaa gccctgccag tctccttttcc ctaggtcatc cccaaggtcc  2040
ttgtgctgag aaactgaggc tcagacagga taaggaccca tacagtgatt gtgaaactcc   2100
agggccaggt gttctcacgt cttttgggac tatggactat agcttgcttc ttacaagcta   2160
tcctgctcac tgcaattgat ctgagggttc agagaagcac agccagtgaa attctgggga   2220 cacggttttcc tgccccgtgc acctctttct gttttgtggt ttggggctca acccaggga   2280 gtttgccttt gtacaagaag tcctgtgtag gcttgaccca gtgaccctgt gacctttggc   2340
atcatccatg ctcctctatg accgctgggt caggcactcc acctagagat tcattacctc   2400
acatggtctg gccggtttc  aatccccttt tccgcacagc ccgcccagt cctttgctaa    2460 gtaattgcta agaagatgag accaagaaac gaaagcaaga taaataatgg aatctcagat   2520
gtacctgacc tgagaccttt gtgggactgg agaagaggag gggcgcgggg cacaaagaca   2580
cagatgatag ggtgtaaaga gggcagaacc tagctgttcc tgatctggga taccccgtct   2640
ccaaaccctg aaacccaact ttccccagaa gtgacactgt atgcgttcac tagagtctaa   2700 cagtccttttt gaaaggacac ccagtgtggc tttgagagct agggcaccta aaatggggga  2760
gggatctagg gaggcgaaag tggaagagaa ccagccagga cctctgtgga gaggggcagg   2820
ggtaggcagg aacacaatgg gagatacctc gctggatcac tgctgggtag gctaggagga   2880
gggtggggca gggcgcctgt ctctgctcct gtggttccag acaacttagt cccacctttg   2940
ctgtttctgc gcgagctcag gaaactcacg gaacttgtac ctcagttgcc ctgctataaa   3000
acagggcaaa gaatctcttc ctgtttcctc gggagcctta agatgctaaa ggggtctgc    3060 ctgagcacat gggcaatgt  actgactggg tgacctcagg tagtcatggt ctctctctct   3120
ctgtgccact tacctctggg cctttgtttc ttctagaaaa cagagcaaaa caacaagact   3180
ggaattatcc ttattgggag agtttcagga acctgacacc agactcagtc actgctgcct   3240
ggacagtcca gtcagacata tgacagtgcg gaagagtgtt tatatctcag tgcagtcaca   3300
ctgggaagag atgggaacta ttgccctaca tcctgtctgt ggtattaaca agagatggag   3360
ggggacacat ctagagcagg gaccaagaag aaagagtcca taagtcaggc tgcctcccat   3420
tatcctgtgg tctggcacat ggtgatcgca cgtctggttc tgtgaggttc cactggcttc   3480
taggacggta ccacagcttg agaggggac  tcagtcccat catccttaag ttcctggaat   3540
gatcttcctg taagatttgc tgtttctgga atctaagaat atactgtttt tacacagggt   3600
ctccctggat agccgagagc catttttctgc tgtgtctatc tgggatggca ggcatccacc   3660
accattctca gcttcttagt ggttttttcag cttgcagtga gtatttagac agacacgcct   3720
ttgatctgta ctcatctgtg tgtggagatg aacaggagtc agacccaaag tttaaggtag   3780
caagggagaa agctccaggc ccaggtgaac ggtcaggact caacagtagc agtgtcagcc   3840
ctgggtcttt ctctagtgtg tcatcagcca ctctttttcct tggggacctg cttagctagg   3900
aatgtctctc caactcaggt ggcctcttac tacagagtcc cagcacacag taccggtcct   3960
caggtcctca aacagggcag atgttcagtg aggtcactac acaaattatc agcacttcct   4020
```

```
ttacagatgg agaaattgag gcacagagaa cgcgcgcgcg cgcgcgcaca cacacacaca    4080
cacacacaca cacacacact agcaccccag gtaccatggt aaagggaggc tccatttgac    4140
aggcatcagg caagtggggc aggccactct aataaaagtg actcagtggc tggcgtgggc    4200
agcggaattt ctaaacatcc tgaaagagcc ggtgaaggga gggagcagag ggaaaggagg    4260
aagaaaaaca agaaagttgg gggaaaagaa agagaggaaa aaaaaaaaaa ccctgaaatt    4320
gaaaacagac acacgcgtcc accctccctg ctccaccgct cccccaccct ccccgccttc    4380
cccaagcttg gccaatcaga atcggccctg cagccttttcc cccaaagtgt gtggtggtgg    4440
tggtggtggg gcagagaaag cccacagtgg tgtgagctct ggggctgtct gtggccacag    4500
tcccggctac cctatctggg acctaggatt gctctgggag taactttgag agagaggaga    4560
acagagagga aacagtccag agccagagcg ggcccagacc agtcgtcagt ctcctgcctg    4620
ccagctagac ctagggcggc ccctcgggct gctccgctcc tcccggagga tgcttttgga    4680
gtgaggaggg gccgggctgc ttctcacccc tgagcaccct ctccattccc ctgattctct    4740
cagggttttc cgcaatcagg ccagcccttc tactgctgtc cgttttttgg gtccagcaaa    4800
ataacagaag acagcgaatt ctgagccgcc accatgagcc aatttgatat attatgtaaa    4860
acaccaccta aggtcctggt tcgtcagttt gtggaaaggt ttgaaagacc ttcaggggaa    4920
aaaatagcat catgtgctgc tgaactaacc tatttatgtt ggatgattac tcataacgga    4980
acagcaatca agagagccac attcatgagc tataatacta tcataagcaa ttcgctgagt    5040
ttcgatattg tcaacaaatc actccagttt aaatacaaga cgcaaaaagc aacaattctg    5100
gaagcctcat taaagaaatt aattcctgct tgggaattta caattattcc ttacaatgga    5160
caaaaacatc aatctgatat cactgatatt gtaagtagtt tgcaattaca gttcgaatca    5220
tcggaagaag cagataaggg aaatagccac agtaaaaaaa tgcttaaagc acttctaagt    5280
gagggtgaaa gcatctggga gatcactgag aaaatactaa attcgtttga gtatacctcg    5340
agatttacaa aaacaaaaac tttataccaa ttcctcttcc tagctacttt catcaattgt    5400
ggaagattca gcgatattaa gaacgttgat ccgaaatcat ttaaattagt ccaaaataag    5460
tatctgggag taataatcca gtgtttagtg acagagacaa agacaagcgt tagtaggcac    5520
atatacttct ttagcgcaag gggtaggatc gatccacttg tatatttgga tgaattttttg    5580 aggaactctg aaccagtcct aaaacgagta aataggaccg gcaattcttc aagcaacaaa    5640
caggaatacc aattattaaa agataactta gtcagatcgt acaacaaggc tttgaagaaa    5700
aatgcgcctt atccaatctt tgctataaag aatggcccaa aatctcacat tggaagacat    5760
ttgatgacct catttctgtc aatgaagggc ctaacggagt tgactaatgt tgtgggaaat    5820
tggagcgata agcgtgcttc tgccgtggcc aggacaacgt atactcatca gataacagca    5880
atacctgatc actacttcgc actagtttct cggtactatg catatgatcc aatatcaaag    5940
gaaatgatag cattgaagga tgagactaat ccaattgagg agtggcagca tatagaacag    6000
ctaaagggta gtgctgaagg aagcatacga tacccccgcat ggaatgggat aatatcacag    6060
gaggtactag actacctttc atcctacata aatagacgca taggaccggt ggaacaaaaa    6120
cttatttctg aagaagatct gtgatagcgg ccgcactcct caggtgcagg ctgcctatca    6180
gaaggtggtg gctggtgtgg ccaatgccct ggctcacaaa taccactgag atctttttcc    6240
ctctgccaaa aattatgggg acatcatgaa gccccttgag catctgactt ctggctaata    6300
aaggaaattt attttcattg caatagtgtg ttggaatttt ttgtgtctct cactcggaag    6360
gacatatggg agggcaaatc atttaaaaca tcagaatgag tatttggttt agagtttggc    6420
```

```
aacatatgcc atatgctggc tgccatgaac aaaggtggct ataaagaggt catcagtata    6480
tgaaacagcc ccctgctgtc cattccttat tccatagaaa agccttgact tgaggttaga    6540
ttttttttat attttgtttt gtgttatttt tttctttaac atccctaaaa ttttccttac    6600
atgttttact agccagattt ttcctcctct cctgactact cccagtcata gctgtccctc    6660
ttctcttatg aagatccctc gacctgcagc ccaagcttgg cgtaatcatg gtcatagctg    6720
tttcctgtgt gaaattgtta tccgctcaca attccacaca acatacgagc cggaagcata    6780
aagtgtaaag cctggggtgc ctaatgagtg agctaactca cattaattgc gttgcgctca    6840
ctgcccgctt tccagtcggg aaacctgtcg tgccagcgga tccgcatctc aattagtcag    6900
caaccatagt cccgccccta actccgccca tcccgcccct aactccgccc agttccgccc    6960
attctccgcc ccatggctga ctaattttt ttatttatgc agaggccgag gccgcctcgg    7020
cctctgagct attccagaag tagtgaggag gcttttttgg aggcctaggc ttttgcaaaa    7080
agctaacttg tttattgcag cttataatgg ttacaaataa agcaatagca tcacaaattt    7140
cacaaataaa gcattttttt cactgcattc tagttgtggt ttgtccaaac tcatcaatgt    7200
atcttatcat gtctggatcc gctgcattaa tgaatcggcc aacgcgcggg gagaggcggt    7260
ttgcgtattg ggcgctcttc cgcttcctcg ctcactgact cgctgcgctc ggtcgttcgg    7320
ctgcggcgag cggtatcagc tcactcaaag gcggtaatac ggttatccac agaatcaggg    7380
gataacgcag gaaagaacat gtgagcaaaa ggccagcaaa aggccaggaa ccgtaaaaag    7440
gccgcgttgc tggcgttttt ccataggctc cgcccccctg acgagcatca caaaaatcga    7500
cgctcaagtc agaggtggcg aaacccgaca ggactataaa gataccaggc gtttccccct    7560
ggaagctccc tcgtgcgctc tcctgttccg accctgccgc ttaccggata cctgtccgcc    7620
tttctccctt cgggaagcgt ggcgctttct caatgctcac gctgtaggta tctcagttcg    7680
gtgtaggtcg ttcgctccaa gctgggctgt gtgcacgaac cccccgttca gcccgaccgc    7740
tgcgccttat ccggtaacta tcgtcttgag tccaacccgg taagacacga cttatcgcca    7800
ctggcagcag ccactggtaa caggattagc agagcgaggt atgtaggcgg tgctacagag    7860
ttcttgaagt ggtggcctaa ctacggctac actagaagga cagtatttgg tatctgcgct    7920
ctgctgaagc cagttacctt cggaaaaaga gttggtagct cttgatccgg caaacaaacc    7980
accgctggta gcggtggttt ttttgtttgc aagcagcaga ttacgcgcag aaaaaaagga    8040
tctcaagaag atcctttgat cttttctacg gggtctgacg ctcagtggaa cgaaaactca    8100
cgttaaggga ttttggtcat gagattatca aaaaggatct tcacctagat ccttttaaat    8160
taaaaatgaa gttttaaatc aatctaaagt atatatgagt aaacttggtc tgacagttac    8220
caatgcttaa tcagtgaggc acctatctca gcgatctgtc tatttcgttc atccatagtt    8280
gcctgactcc ccgtcgtgta gataactacg atacgggagg gcttaccatc tggccccagt    8340
gctgcaatga taccgcgaga cccacgctca ccggctccag atttatcagc aataaaccag    8400
ccagccggaa gggccgagcg cagaagtggt cctgcaactt tatccgcctc catccagtct    8460
attaattgtt gccgggaagc tagagtaagt agttcgccag ttaatagttt gcgcaacgtt    8520
gttgccattg ctacaggcat cgtggtgtca cgctcgtcgt ttggtatggc ttcattcagc    8580
tccggttccc aacgatcaag gcgagttaca tgatccccca tgttgtgcaa aaaagcggtt    8640
agctccttcg gtcctccgat cgttgtcaga agtaagttgg ccgcagtgtt atcactcatg    8700
gttatggcag cactgcataa ttctcttact gtcatgccat ccgtaagatg cttttctgtg    8760
```

| | |
|---|---:|
| actggtgagt actcaaccaa gtcattctga aatagtgta tgcggcgacc gagttgctct | 8820 |
| tgcccggcgt caatacggga taataccgcg ccacatagca aactttaaa agtgctcatc | 8880 |
| attggaaaac gttcttcggg gcgaaaactc tcaaggatct taccgctgtt gagatccagt | 8940 |
| tcgatgtaac ccactcgtgc acccaactga tcttcagcat cttttacttt caccagcgtt | 9000 |
| tctgggtgag caaaaacagg aaggcaaaat gccgcaaaaa agggaataag ggcgacacgg | 9060 |
| aaatgttgaa tactcatact cttccttttt caatattatt gaagcattta tcagggttat | 9120 |
| tgtctcatga gcggatacat atttgaatgt atttagaaaa ataaacaaat aggggttccg | 9180 |
| cgcacatttc cccgaaaagt gccacctg | 9208 |

```
<210> SEQ ID NO 2
<211> LENGTH: 12710
<212> TYPE: DNA
<213> ORGANISM: Artificial Sequence
<220> FEATURE:
<223> OTHER INFORMATION: pcDNA5 CSPG4cre
<220> FEATURE:
<221> NAME/KEY: misc_feature
<222> LOCATION: (3377)..(3377)
<223> OTHER INFORMATION: n is a, c, g, or t
<220> FEATURE:
<221> NAME/KEY: misc_feature
<222> LOCATION: (3403)..(3403)
<223> OTHER INFORMATION: n is a, c, g, or t
```

<400> SEQUENCE: 2

| | |
|---|---:|
| gacggatcgg gagatctccc gatccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaactt aagcttggta ccgtcgaggg atcttcataa gagaagaggg acagctatga | 960 |
| ctgggagtag tcaggagagg aggaaaaatc tggctagtaa aacatgtaag gaaaattta | 1020 |
| gggatgttaa agaaaaaaat aacacaaaac aaaatataaa aaaatctaa cctcaagtca | 1080 |
| aggcttttct atgaataag gaatggacag caggggctg tttcatatac tgatgacctc | 1140 |
| tttatagcca cctttgttca tggcagccag catatggcat atgttgccaa actctaaacc | 1200 |
| aaatactcat tctgatgttt taaatgattt gccctcccat atgtccttcc gagtgagaga | 1260 |
| cacaaaaaat tccaacacac tattgcaatg aaaataaatt tccttttatta gccagaagtc | 1320 |
| agatgctcaa ggggcttcat gatgtcccca taatttttgg cagagggaaa aagatctcag | 1380 |

```
tggtatttgt gagccagggc attggccaca ccagccacca ccttctgata ggcagcctgc    1440
acctgaggag tgcgctatca cagatcttct tcagaaataa gttttttgttc caccggtcca   1500 tcgccatctt ccagcaggcg caccattgcc cctgtttcac tatccaggtt acggatatag   1560
ttcatgacaa tatttacatt ggtccagcca ccagcttgca tgatctccgg tattgaaact   1620
ccagcgcggg ccatatctcg cgcggctccg acacgggcac tgtgtccaga ccaggccagg   1680
tatctctgac cagagtcatc cttagcgccg taaatcaatc gatgagttgc ttcaaaaatc   1740
ccttccaggg cgcgagttga tagctggctg gtggcagatg gcgcggcaac accattttt    1800 ctgacccggc aaaacaggta gttattcgga tcatcagcta caccagagac ggaaatccat   1860
cgctcgacca gtttagttac ccccaggcta agtgccttct ctacacctgc ggtgctaacc   1920
agcgttttcg ttctgccaat atggattaac attctcccac cgtcagtacg tgagatatct   1980
ttaaccctga tcctggcaat ttcggctata cgtaacaggg tgttataagc aatccccaga   2040
aatgccagat tacgtatatc ctggcagcga tcgctatttt ccatgagtga acgaacctgg   2100
tcgaaatcag tgcgttcgaa cgctagagcc tgttttgcac gttcaccggc atcaacgttt   2160
tcttttcgga tccgccgcat aaccagtgaa acagcattgc tgtcacttgg tcgtggcagc   2220
ccggaccgac gatgaagcat gtttagctgg cccaaatgtt gctggatagt ttttactgcc   2280
agaccgcgcg cctgaagata tagaagataa tcgcgaacat cttcaggttc tgcgggaaac   2340
catttccggt tattcaactt gcaccatgcc gcccacgacc ggcaaacgga cagaagcatt   2400
ttccaggtat gctcagaaaa cgcctggcga tccctgaaca tgtccatcag gttcttgcga   2460
acctcatcac tcgttgcatc gaccggtaat gcaggcaaat tttggtgtac ggtcagtaaa   2520
ttggccatgg tggcggctca gtcgacgttt gaagttccta tactttctag aaataggaa    2580 cttcgttcct cgcgagctgc agacttactc aagccatggt ggctagcttg cggaattcta   2640
ttaagggttc cggatcagct tgatggggat ccagacatga taagatacat tgatgagttt   2700
ggacaaacca caactagaat gcagtgaaaa aaatgcttta tttgtgaaat ttgtgatgct   2760
attgctttat ttgtaaccat tataagctgc aataaacaag ttaacaacaa caattgcatt   2820 catttatgt ttcaggttca gggggaggtg tgggaggttt tttaaagcaa gtaaaacctc    2880
tacaaatgtg gtatggctga ttatgatcct ctagagtcgc agatccagac atgataagat   2940
acattgatga gtttggacaa accacaacta gaatgcagtg aaaaaaatgc tttatttgtg   3000
aaatttgtga tgctattgct ttatttgtaa ccattataag ctgcaataaa caagttaaca   3060
acaacaattg cattcatttt atgtttcagg ttcaggggga ggtgtgggag gtttttaaa    3120 gcaagtaaaa cctctacaaa tgtggtatgg ctgattatga tcctctagag tcgcagatcc   3180
agacatgata agatacattg atgagtttgg acaaaccaca actagaatgc agtgaaaaaa   3240
atgctttatt tgtgaaattt gtgatgctat tgctttattt gtaaccatta agctgcaa     3300 taaacaagtt aacaacaaca attgcattca ttttatgttt caggttcagg ggaggtgtg    3360 ggaggttttt taaagcnagt aaaacctcta caaaatgtgg tanggctgat tatgatcctc   3420
tagagtcgca gatcctctag agtcgcagat ctgcaagctt tcatttattc atcgcgatga   3480
agttcctata ctttctagag aataggaact tcgcggccgc tgggtgcctg gacttgtaag   3540
gcgaaggaac agagcgtgct gaatctggac agcaccgagt cgcaagtcgc aagtcgcaat   3600
tcaagtccaa agtcgaggga gcagggctcc tcgcacgggc tagggcgcaa gggctgtcca   3660
gtacttaact ccgggggcgg ggcaggcgcc agacccgcgc ttagatttcg gcgggggct    3720
```

```
ccctctgtct gctcccacct ccaactttct taaaggggcc gtgctgggct cttgctcctg    3780
gttaggattg aaggacctt t cctgccaagg cagacccatg ccccatttta agggtttggg   3840
acaatgtctc ttaagtcttt agaccccag  aactctgtgg acaggatctc ttgagaacgg    3900
gaaataaaag tgagagctgc cagccctctt ctgcccttgc ggtgatgtag gggtttaggt    3960
gccttcaagg tcacaggtcc ccgaggattc cactaaagca gaccgctagg cagggctctg    4020
ggtttgccct tctcttttcca cagactgtac attctctgcc tgtaaagaca agaggtctgg   4080
atcttgtggt gcagaagctc agccctgtgg taacacatgc ttcaaaacaa ccctgcaagg    4140
taggggctga gcaccctt cc cttcattttg tggaggagga gcccagctca gaatccaagg   4200
tcaaaggtag tgcctggcca tttcctgcca ggatcccagg cctcctgacc cccaaatctt    4260
ggtgttttca cttgccccac cacctcctgg aaatctggcc ctggatttag ctcctaccta    4320
acagcttcag gctgggcct  tctcctcctg gctccttccc aggcaagagc ctgcctagtc    4380
ccaaccagga gctggaaaaa gcagagttac tgtggctttt ccccgtgcct gtgtttggcc    4440
agccccagct gcattgggac ctggcctggg tttttttctag agacgcata  gaggaacact   4500
cccgttcctc tcttctttca cgcatatccc tccactgggc tccctgctgt gcccacgttc    4560
cactgtgcac cctcttt cca atccttaccc ctgagcagca acaatcatag cacaagtcca    4620
gcgtctcatg acttctgata gaaccgagcc ccatttcgat agagaaactg aggctgagag    4680
ggattaaagg gcctggtga  gttgatccag gcgagggcaa gccgaatcat tgagcccatg    4740
ctctgtgctc ttactaccat gcctggtctg atgtgttctt gatcccaatt ctcctacttg    4800
actggccttt aactactcct ttttttcctg tggttcagtt tttcacttac aagttttgaat   4860
ttataagcat taagtgtttt aatatgtctc aaatgcctac cttagggcct ggcatacagt    4920
aggtgttcaa ctcatatcgc cttttcttct tcctctctca ttctgcacat cccagtactt    4980
cacggtttgt atacaactac tgcacatcct cccct tgatg gagggtcttc tgtgaacctt    5040
tgactttccc ctccgtaggc agttgcatac agtaggtgtt caataagtac ctgttaaggt    5100
ggactaagaa gctgattgtt gctattctat ggggacttag acagacttag gaactatcca    5160
ggcaccctgg ggaacctgac acagtgagcc tatgccttgt ttcttgtttt ccttcttctg    5220
agtcagcaca acacttggtc ctcattaagg gccaattact gtccaaatat ggatccaggg    5280
tttgggaggg gaggcttctt ggaaggttgg ggaagaagag ttctctcttt aagaatgaga    5340
gggaggggaa atgtttgtct ttttatgaat tgggaactag agaggagacg tgcaccatcc    5400
cataccgccc atcttctggc atcttgctcg gccccctaccc acagatttat tgcccacca    5460
ccaccaggaa tcacttctct gtctggggag cctccagact agtagctgca gcccagccca    5520
cagctgagat ttaagacagg atgagctcag agcctcccca gccttgctgc ccgtgggtt     5580
gagaaacaga cctagaaaaa gaatacaaca agcactgtgt tcatgaccca gcttgtgcat    5640
ctctgccggg gtttcccagt ctgtaaaaca tttaccaggg ggaatgccta ggtggcagaa    5700
cacttgccta gcatgcacaa ggccctggat tcactctcta gcactggatc tggggaaggg    5760
ttggagtagg atggggatgt agctcagttg atagagtgcc tgctgagcat caaaaagccc    5820
tgggtttgct ctgtagcagt gcataaaacc tggacatggt gtgaagaggt agctctgcaa    5880
ttaaaagtgc tcactgcttt tgcataggac ctgaatttgg ttcccagcac ccacattgag    5940
gggctcacaa ctacctgtag ctctagttcc aggggctctg atatcctctt ctagattcca    6000
taggtacctg tatacataca tgtcatacat tcacataaat acacacaaaa ttaaattcaa    6060
ttataatgaa ccttattttt aaaaaaaaga tttatttatt tatttatgta tataaataca    6120
```

```
ctgtcttcat gcacaccaga agagggcatc agatcccatt acagatgtgg ttgctgttgt    6180
gagccaccat gtgggaattg aactcaggac ctctggaaga gtagccagtg ctcttacccg    6240
ctgagccatc acaccgcacc ccctgaaatg aatcttaaaa aaaaaaaaaa acaaggacag    6300
aaaagtggac atagctacat aagcttttaa tcctaacact taggaggtgg aggcaagaga    6360
acagaaaagc aaggtcattt tcaactataa agctacttcc agactagcct gaagtggggg    6420
aagaccgaga gagagcgaga gagagagaga cagagacaga gacagagaga cagagagaga    6480
gacacacaca cagagagaaa ataagaatca ttcacctggg aaataaacat gttcatggac    6540
aaaagagaaa accgaggctc tcagtccttt agaccagacc actggggctc tgggtattca    6600
tgcttgccct ctgttagtct gtagcgtgag gcttgaaccc cggacagaag ctcagcagag    6660
acatgaggat tgaggccccc tgtagcttta gaacgattga ccatctccca ctgactcaga    6720
gtgtgctgtt gggtgggta gtgtcagctc cccagtcgtt ttcacccag cctcttgggc      6780 agagctgagc caaacctccc tggcatcctc agggttgact cttgcctccc ttctgcctgc    6840
taacctttgc catgatttcc cttgacttgg gtcgaccaga cacacaccgt gactactcca    6900
gtgccctatc tccctggtca tgtcttacct tcccccgaca ggtgcttttc tgtctgaaaa    6960
ctctatggag tcttctccct agctagacca tggggtttta actcagtgct ttccccaccc    7020
tctagaatga caccgctcca caggacagga caccccagtga gacaagtgaa gatgatgact    7080
ctgttttttt gtttatttgt tttgtttgt tttttctttt tcttttttt ttcgagacag     7140 ggtttctctg tatagtcctg gctgtcctgg aactcacttt gtagaccagg ctggcctcga    7200
actcagaaat ctgcctgcct ctgcctccca agtgctggga ttaaaggcgt gcgccaccac    7260
cgcccggctg aagatgatga ctctgaacat ctcacctatc aatcagagga ttacaaatcc    7320
tctgaagctt ccatgacccc caagcactct aggaaaatga acaacagac agacaaacaa     7380 tttctccttc cccaacaatg tgtagctctg caggctggct aggctctttt ggtcactttt    7440
actagctccc atccccagtg catctgggac taagcatgcc cgctttggca gtggcagcca    7500
caccctgccc tcagcctggg tgttttgcac tctgaccgac tggctccacc caaggagcct    7560
gtggccaaag ccagcctgct ggtaaatggc gtgggcttct gccctcaaag gggtggtgtc    7620
tgagcagcgt tgttcttcaa ctgcttggaa cctgcccttta gggaactggc cctttgccat   7680
acaggacaca gaccgcagac taccctgtgc aaggggacat gggctttagg cattggctcc    7740
tcggctctac agcctcagaa ccagaaactt ctctgcagca gcctcaggct aagcttctgc    7800
taggagtagt ctcgctccca ctttttggcc aaggagcctg tgaggctcct tcaagtgcag    7860
gcagccaggc tcaggctagt cccagcaatt acacttcaga agctgaaaag ttgtctttgc    7920
tggtttggga gcaaggctgt gaatggagg cccgtgggga gctttgccta tctagcctgg     7980
gtgggcttta agccacgtct gtaccatatt gggccgatag cgtgggggca ggggggggtt    8040
accctctcgg ggcttctcgg attctccaga acaggctctc ccctgccaca ccatgtccgc    8100
aaagacttgt ggcttcagtg ctgtgaccaa gctggccaca gctgactccc tttgggatgc    8160
gctatttcta aatattagtt catgctgtta acccttgcca tacagtccta atggacattg    8220
gaagcctgca gggacaggct tcggaaggag gctgaatggg cccagctag gtggaaaatc     8280 tgtgagtata ctcactcagg gtctggcatg ggttgggcac ctttgagggg ctcttttggg    8340
ttcctgcaag gatgagaaat acctgcttgg gcctgggacc aaagcttgca atgggcttta    8400
gatgtggatc tgagctggcg gtctgggcag ggaaatggaa agaatgtggg gtgaggagcc    8460
```

```
aggagttggg tcttgccaat cctcttctgt gtgcctcaca tgagtcatgt cacctatctg   8520
tgcttttccc tcatctgtac agagccacta tggtacggga tgatggcctc cagcagagat   8580
actgaggctt tgtaaactga agggcagagc ctggaggttc cgccactcga gtctagaggg   8640
cccgtttaaa cccgctgatc agcctcgact gtgccttcta gttgccagcc atctgttgtt   8700
tgcccctccc ccgtgccttc cttgaccctg aaggtgcca ctcccactgt cctttcctaa    8760
taaaatgagg aaattgcatc gcattgtctg agtaggtgtc attctattct gggggtggg    8820
gtggggcagg acagcaaggg ggaggattgg gaagacaata gcaggcatgc tggggatgcg   8880
gtgggctcta tggcttctga ggcggaaaga accagctggg gctctagggg gtatccccac   8940
gcgccctgta gcggcgcatt aagcgcggcg ggtgtggtgg ttacgcgcag cgtgaccgct   9000
acacttgcca gcgccctagc gcccgctcct ttcgctttct tcccttcctt tctcgccacg   9060
ttcgccggct ttccccgtca agctctaaat cggggtccc tttagggttc cgatttagtg    9120
ctttacggca cctcgacccc aaaaaacttg attagggtga tggttcacgt acctagaagt   9180
tcctattccg aagttcctat tctctagaaa gtataggaac ttccttggcc aaaaagcctg   9240
aactcaccgc gacgtctgtc gagaagtttc tgatcgaaaa gttcgacagc gtctccgacc   9300
tgatgcagct ctcggagggc gaagaatctc gtgctttcag cttcgatgta ggagggcgtg   9360
gatatgtcct gcgggtaaat agctgcgccg atggtttcta caaagatcgt tatgtttatc   9420
ggcactttgc atcggccgcg ctcccgattc cggaagtgct tgacattggg gaattcagcg   9480
agagcctgac ctattgcatc tcccgccgtg cacagggtgt cacgttgcaa gacctgcctg   9540
aaaccgaact gcccgctgtt ctgcagccgg tcgcggaggc catggatgcg atcgctgcgg   9600
ccgatcttag ccagacgagc gggttcggcc cattcggacc gcaaggaatc ggtcaataca   9660
ctacatggcg tgatttcata tgcgcgattg ctgatcccca tgtgtatcac tggcaaactg   9720
tgatggacga caccgtcagt gcgtccgtcg cgcaggctct cgatgagctg atgctttggg   9780
ccgaggactg ccccgaagtc cggcacctcg tgcacgcgga tttcggctcc aacaatgtcc   9840
tgacggacaa tggccgcata acagcggtca ttgactggag cgaggcgatg ttcggggatt   9900
cccaatacga ggtcgccaac atcttcttct ggaggccgtg gttggcttgt atggagcagc   9960
agacgcgcta cttcgagcgg aggcatccgg agcttgcagg atcgccgcgg ctccgggcgt   10020
atatgctccg cattggtctt gaccaactct atcagagctt ggttgacggc aatttcgatg   10080
atgcagcttg gcgcagggt cgatgcgacg caatcgtccg atccggagcc gggactgtcg   10140
ggcgtacaca aatcgcccgc agaagcgcgg ccgtctggac cgatggctgt gtagaagtac   10200
tcgccgatag tggaaaccga cgccccagca ctcgtccgag ggcaaaggaa tagcacgtac   10260
tacgagattt cgattccacc gccgccttct atgaaaggtt gggcttcgga atcgttttcc   10320
gggacgccgg ctggatgatc ctccagcgcg gggatctcat gctggagttc ttcgcccacc   10380
ccaacttgtt tattgcagct tataatggtt acaaataaag caatagcatc acaaatttca   10440
caaataaagc atttttttca ctgcattcta gttgtggttt gtccaaactc atcaatgtat   10500
cttatcatgt ctgtataccg tcgacctcta gctagagctt ggcgtaatca tggtcatagc   10560
tgtttcctgt gtgaaattgt tatccgctca caattccaca acatacga gccggaagca    10620
taaagtgtaa agcctggggt gcctaatgag tgagctaact cacattaatt gcgttgcgct   10680
cactgcccgc tttccagtcg ggaaacctgt cgtgccagct gcattaatga atcggccaac   10740
gcgcggggag aggcggtttg cgtattgggc gctcttccgc ttcctcgctc actgactcgc   10800
tgcgctcggt cgttcggctg cggcgagcgg tatcagctca ctcaaaggcg gtaatacggt   10860
```

```
tatccacaga atcagggat aacgcaggaa agaacatgtg agcaaaaggc cagcaaaagg    10920
ccaggaaccg taaaaaggcc gcgttgctgg cgttttttcca taggctccgc cccctgacg    10980
agcatcacaa aaatcgacgc tcaagtcaga ggtggcgaaa cccgacagga ctataaagat    11040
accaggcgtt tccccctgga agctccctcg tgcgctctcc tgttccgacc ctgccgctta    11100
ccggatacct gtccgccttt ctcccttcgg aagcgtggc gctttctcat agctcacgct    11160
gtaggtatct cagttcggtg taggtcgttc gctccaagct gggctgtgtg cacgaacccc    11220
ccgttcagcc cgaccgctgc gccttatccg gtaactatcg tcttgagtcc aacccggtaa    11280
gacacgactt atcgccactg gcagcagcca ctggtaacag gattagcaga gcgaggtatg    11340
taggcggtgc tacagagttc ttgaagtggt ggcctaacta cggctacact agaaggacag    11400
tatttggtat ctgcgctctg ctgaagccag ttaccttcgg aaaaagagtt ggtagctctt    11460
gatccggcaa acaaaccacc gctggtagcg gtggtttttt tgtttgcaag cagcagatta    11520
cgcgcagaaa aaaggatct caagaagatc ctttgatctt ttctacgggg tctgacgctc    11580
agtggaacga aaactcacgt taagggattt tggtcatgag attatcaaaa aggatcttca    11640
cctagatcct tttaaattaa aaatgaagtt ttaaatcaat ctaaagtata tatgagtaaa    11700
cttggtctga cagttaccaa tgcttaatca gtgaggcacc tatctcagcg atctgtctat    11760
ttcgttcatc catagttgcc tgactccccg tcgtgtagat aactacgata cgggagggct    11820
taccatctgg ccccagtgct gcaatgatac cgcgagaccc acgctcaccg gctccagatt    11880
tatcagcaat aaaccagcca gccggaaggg ccgagcgcag aagtggtcct gcaactttat    11940
ccgcctccat ccagtctatt aattgttgcc gggaagctag agtaagtagt tcgccagtta    12000
atagtttgcg caacgttgtt gccattgcta caggcatcgt ggtgtcacgc tcgtcgtttg    12060
gtatggcttc attcagctcc ggttcccaac gatcaaggcg agttacatga tcccccatgt    12120
tgtgcaaaaa agcggttagc tccttcggtc tccgatcgt tgtcagaagt aagttggccg    12180
cagtgttatc actcatggtt atggcagcac tgcataattc tcttactgtc atgccatccg    12240
taagatgctt ttctgtgact ggtgagtact caaccaagtc attctgagaa tagtgtatgc    12300
ggcgaccgag ttgctcttgc ccggcgtcaa tacgggataa taccgcgcca catagcagaa    12360
ctttaaaagt gctcatcatt ggaaaacgtt cttcggggcg aaaactctca aggatcttac    12420
cgctgttgag atccagttcg atgtaaccca ctcgtgcacc caactgatct tcagcatctt    12480
ttactttcac cagcgtttct gggtgagcaa aaacaggaag gcaaaatgcc gcaaaaaagg    12540
gaataagggc gacacggaaa tgttgaatac tcatactctt cctttttcaa tattattgaa    12600
gcatttatca gggttattgt ctcatgagcg gatacatatt tgaatgtatt tagaaaaata    12660
aacaaatagg ggttccgcgc acatttcccc gaaaagtgcc acctgacgtc                12710
```

<210> SEQ ID NO 3
<211> LENGTH: 17021
<212> TYPE: DNA
<213> ORGANISM: Artificial Sequence
<220> FEATURE:
<223> OTHER INFORMATION: Ai14

<400> SEQUENCE: 3

```
ccgcggcagg ccctccgagc gtggtggagc cgttctgtga cagccgggg tacgagtcgt        60
gacgctggaa ggggcaagcg ggtggtgggc aggaatgcgg tccgccctgc agcaaccgga      120
gggggaggga gaagggagcg gaaaagtctc caccggacgc ggccatggct cgggggggg      180
```

-continued

```
ggggcagcgg aggagcgctt ccggccgacg tctcgtcgct gattggcttc ttttcctccc    240
gccgtgtgtg aaaacacaaa tggcgtgttt tggttggcgt aaggcgcctg tcagttaacg    300
gcagccggag tgcgcagccg ccggcagcct cgctctgccc actgggtggg gcggaggta     360
ggtggggtga ggcgagctgg acgtgcgggc gcggtcggcc tctggcgggg cggggggggg    420
gggggggggt cagcgaaagt agctcgcgcg cgagcggccg cccaccctcc ccttcctctg    480
gggagtcgt tttacccgcc gccggccggg cctcgtcgtc tgattggctc tcggggccca     540
gaaaactggc ccttgccatt ggctcgtgtt cgtgcaagtt gagtccatcc gccggccagc    600
ggggcggcg aggaggcgct cccaggttcc ggccctcccc tcggcccgc gccgcagagt      660
ctggccgcgc gcccctgcgc aacgtggcag gaagcgcgcg ctggggggcgg ggacgggcag   720
tagggctgag cggctgcggg gcgggtgcaa gcacgtttcc gacttgagtt gcctcaagag    780
gggcgtgctg agccagacct ccatcgcgca ctccggggag tggagggaag gagcgagggc    840
tcagttgggc tgttttggag gcaggaagca cttgctctcc caaagtcgct ctgagttgtt    900
atcagtaagg gagctgcagt ggagtaggcg gggagaaggc cgcacccttc tccggagggg    960
ggagggagt gttgcaatac ctttctggga gttctctgct gcctcctggc ttctgaggac    1020
cgccctgggc ctgggagaat cccttccccc tcttccctcg tgatctgcaa ctccagtctt   1080
tctagcctta attaaccgtt taaacaattc tgcaggaatc tagttattaa tagtaatcaa   1140
ttacggggtc attagttcat agcccatata tggagttccg cgttacataa cttacggtaa   1200
atggcccgcc tggctgaccg cccaacgacc cccgcccatt gacgtcaata atgacgtatg   1260
ttcccatagt aacgccaata gggactttcc attgacgtca atgggtggag tatttacggt   1320
aaactgccca cttggcagta catcaagtgt atcatatgcc aagtacgccc cctattgacg   1380
tcaatgacgg taaatggccc gcctggcatt atgcccagta catgacctta tgggactttc   1440
ctacttggca gtacatctac gtattagtca tcgctattac catggtcgag gtgagcccca   1500
cgttctgctt cactctcccc atctcccccc cctccccacc cccaattttg tatttattta   1560
tttttaatt attttgtgca gcgatggggg cggggggggg gggggsgcg cgccaggcgg     1620
ggcggggcgg ggcgaggggc ggggcgggc gaggcggaga ggtgcggcgg cagccaatca    1680
gagcggcgcg ctccgaaagt tccttttat ggcgaggcgg cggcggcggc ggccctataa    1740
aaagcgaagc gcgcggcggg cgcggccggg agtcgctgcg cgctgccttc gccccgtgcc   1800
ccgctccgcc gccgcctcgc gccgcccgcc ccggctctga ctgaccgcgt tactcccaca   1860
ggtgagcggg cgggacggcc cttctcctcc gggctgtaat tagcgcttgg tttaatgacg   1920
gcttgtttct tttctgtggc tgcgtgaaag ccttgagggg ctccgggagg gccctttgtg   1980
cggggggagc ggctcggggg gtgcgtgcgt gtgtgtgtgc gtggggagcg ccgcgtgcgg   2040
ctccgcgctg cccggcggct gtgagcgctg cgggcgcggc gcgggctttt gtgcgctccg   2100
cagtgtgcgc gaggggagcg cggcggggg cggtgccccg cggtgcgggg gggctgcga    2160
ggggaacaaa ggctgcgtgc ggggtgtgtg cgtgggggg tgagcagggg gtgtgggcgc    2220
gtcggtcggg ctgcaacccc ccctgcaccc ccctccccga gttgctgagc acggcccggc   2280
ttcgggtgcg gggctccgta cggggcgtgg cgcggggctc gccgtgccgg gcggggggtg   2340
gcggcaggtg ggggtgccgg gcggggcggg gccgcctcgg gccggggagg gctcggggga   2400
ggggcgcggc ggccccggga gcgcggcgg ctgtcgaggc gcggcgagcc gcagccattg    2460
ccttttatgg taatcgtgcg agagggcgca gggacttcct ttgtcccaaa tctgtgcgga   2520
gccgaaatct gggaggcgcc gccgcacccc ctctagcggg cgcggggcga agcggtgcgg   2580
```

-continued

```
cgccggcagg aaggaaatgg gcggggaggg ccttcgtgcg tcgccgcgcc gccgtcccct    2640
tctccctctc cagcctcggg gctgtccgcg ggggacggc tgccttcggg ggggacgggg     2700
cagggcgggg ttcggcttct ggcgtgtgac cggcggctct agagcctctg ctaaccatgt    2760
tcatgccttc ttcttttcc tacagctcct gggcaacgtg ctggttattg tgctgtctca     2820
tcattttggc aaagaattga tttgataccg cgggccctaa aagttccta ttctctagaa     2880 agtataggaa cttcgtcgac atttaaatca tttaaatata acttcgtata atgtatgcta    2940
tacgaagtta ttcgcgatga ataaatgaaa gcttgcagat ctgcgactct agaggatctg    3000
cgactctaga ggatcataat cagccatacc acatttgtag aggttttact tgctttaaaa    3060
aacctcccac acctccccct gaacctgaaa cataaaatga atgcaattgt tgttgttaac    3120
ttgtttattg cagcttataa tggttacaaa taaagcaata gcatcacaaa tttcacaaat    3180
aaagcatttt tttcactgca ttctagttgt ggtttgtcca aactcatcaa tgtatcttat    3240
catgtctgga tctgcgactc tagaggatca taatcagcca taccacattt gtagaggttt    3300
tacttgcttt aaaaaacctc ccacacctcc ccctgaacct gaaacataaa atgaatgcaa    3360
ttgttgttgt taacttgttt attgcagctt ataatggtta caaataaagc aatagcatca    3420
caaatttcac aaataaagca ttttttcac tgcattctag ttgtggtttg tccaaactca     3480
tcaatgtatc ttatcatgtc tggatctgcg actctagagg atcataatca gccataccac    3540
atttgtagag gttttacttg ctttaaaaaa cctcccacac ctcccccgta acctgaaaca    3600
taaaatgaat gcaattgttg ttgttaactt gtttattgca gcttataatg ttacaaata    3660 aagcaatagc atcacaaatt tcacaaataa agcatttttt tcactgcatt ctagttgtgg    3720
tttgtccaaa ctcatcaatg tatcttatca tgtctggatc cccatcaagc tgatccggaa    3780
cccttaatat aacttcgtat aatgtatgct atacgaagtt attaggtccc tcgacctgca    3840
gcccaagcta atcgaattc ggccggcctt gtacgcgtta agtgcaacac gatcccgcca     3900
ccatggtgag caagggcgag gaggtcatca aagagttcat gcgcttcaag gtgcgcatgg    3960
agggctccat gaacggccac gagttcgaga tcgagggcga gggcgagggc cgccctacg     4020 agggcaccca gaccgccaag ctgaaggtga ccaagggcgg cccctgccc ttcgcctggg     4080 acatcctgtc cccccagttc atgtacggct ccaaggcgta cgtgaagcac ccgccgaca     4140 tccccgatta caagaagctg tccttccccg agggcttcaa gtgggagcgc gtgatgaact    4200
tcgaggacgg cggtctggtg accgtgaccc aggactcctc cctgcaggac ggcacgctga    4260
tctacaaggt gaagatgcgc ggcaccaact tccccccga cggccccgta atgcagaaga    4320
agaccatggg ctgggaggcc tccaccgagc gcctgtaccc ccgcgacggc gtgctgaagg    4380
gcgagatcca ccaggccctg aagctgaagg acggcggcca ctacctggtg gagttcaaga    4440
ccatctacat ggccaagaag cccgtgcaac tgcccggcta ctactacgtg gacaccaagc    4500
tggacatcac ctcccacaac gaggactaca ccatcgtgga acagtacgag cgctccgagg    4560
gccgccacca cctgttcctg gggcatggca ccggcagcac cggcagcggc agctccggca    4620
ccgcctcctc cgaggacaac aacatggccg tcatcaaaga gttcatgcgc ttcaaggtgc    4680
gcatggaggg ctccatgaac ggccacgagt tcgagatcga gggcgagggc gagggccgcc    4740
cctacgaggg cacccagacc gccaagctga aggtgaccaa gggcggcccc ctgcccttcg    4800
cctgggacat cctgtccccc cagttcatgt acggctccaa ggcgtacgtg aagcaccccg    4860
ccgacatccc cgattacaag aagctgtcct tccccgaggg cttcaagtgg gagcgcgtga    4920
```

```
tgaacttcga ggacggcggt ctggtgaccg tgacccagga ctcctccctg caggacggca    4980
cgctgatcta caaggtgaag atgcgcggca ccaacttccc ccccgacggc cccgtaatgc    5040
agaagaagac catgggctgg gaggcctcca ccgagcgcct gtaccccgc gacggcgtgc     5100 tgaagggcga gatccaccag gccctgaagc tgaaggacgg cggccactac ctggtggagt    5160
tcaagaccat ctacatggcc aagaagcccg tgcaactgcc cggctactac tacgtggaca    5220
ccaagctgga catcacctcc cacaacgagg actacaccat cgtggaacag tacgagcgct    5280
ccgagggccg ccaccacctg ttcctgtacg gcatggacga gctgtacaag taagaattgt    5340
gttgcactta acgcgtacaa ggccggcccc gcaggaattc gatatcaagc ttatcgataa    5400
tcaacctctg gattacaaaa tttgtgaaag attgactggt attcttaact atgttgctcc    5460
ttttacgcta tgtggatacg ctgctttaat gcctttgtat catgctattg cttcccgtat    5520
ggctttcatt ttctcctcct tgtataaatc ctggttgctg tctctttatg aggagttgtg    5580
gcccgttgtc aggcaacgtg gcgtggtgtg cactgtgttt gctgacgcaa ccccactgg    5640 ttggggcatt gccaccacct gtcagctcct ttccgggact ttcgctttcc cctccctat    5700 tgccacggcg gaactcatcg ccgcctgcct tgcccgctgc tggacagggg ctcggctgtt    5760
gggcactgac aattccgtgg tgttgtcggg gaaatcatcg tcctttcctt ggctgctcgc    5820
ctgtgttgcc acctggattc tgcgcgggac gtccttctgc tacgtccctt cggccctcaa    5880
tccagcggac cttccttccc gcggcctgct gccggctctg cggcctcttc cgcgtcttcg    5940
ccttcgccct cagacgagtc ggatctccct ttgggccgcc tccccgcatc gataccgtcg    6000
acctcgacct cgactgtgcc ttctagttgc cagccatctg ttgtttgccc ctccccgtg    6060 ccttccttga ccctggaagg tgccactccc actgtccttt cctaataaaa tgaggaaatt    6120
gcatcgcatt gtctgagtag gtgtcattct attctggggg gtggggtggg caggacagc    6180 aaggggagg attgggaaga caatggcagg catgctgggg aactagtggt gccagggcgt    6240
gcccttgggc tccccgggcg cggcggccgc atcgaattct accgggtagg ggaggcgctt    6300
ttcccaaggc agtctggagc atgcgcttta gcagccccgc tgggcacttg gcgctacaca    6360
agtggcctct ggcctcgcac acattccaca tccaccggta ggcgccaacc ggctccgttc    6420
tttggtggcc ccttcgcgcc accttctact cctcccctag tcaggaagtt cccccccgcc    6480
ccgcagctcg cgtcgtgcag gacgtgacaa atggaagtag cacgtctcac tagtctcgtg    6540
cagatggaca gcaccgctga gcaatggaag cgggtaggcc tttggggcag cggccaatag    6600
cagctttgct ccttcgcttt ctgggctcag aggctgggaa ggggtgggtc cggggcggg    6660 ctcagggcg ggctcagggg cggggcgggc gcccgaaggt cctccggagg cccggcattc    6720
tgcacgcttc aaaagcgcac gtctgccgcg ctgttctcct cttcctcatc tccgggcctt    6780
tcgacctgca atcgccgcta gcgaagttcc tattctctag aaagtatagg aacttcgcca    6840
ccatgggatc ggccattgaa caagatggat tgcacgcagg ttctccggcc gcttgggtgg    6900
agaggctatt cggctatgac tgggcacaac agacaatcgg ctgctctgat gccgccgtgt    6960
tccggctgtc agcgcagggg cgcccggttc tttttgtcaa gaccgacctg tccggtgccc    7020
tgaatgaact gcaggacgag gcagcgcggc tatcgtggct ggccacgacg ggcgttcctt    7080
gcgcagctgt gctcgacgtt gtcactgaag cgggaaggga ctggctgcta ttgggcgaag    7140
tgccggggca ggatctcctg tcatctcacc ttgctcctgc cgagaaagta tccatcatgg    7200
ctgatgcaat gcggcggctg catacgcttg atccggctac ctgcccattc gaccaccaag    7260
cgaaacatcg catcgagcga gcacgtactc ggatggaagc cggtcttgtc gatcaggatg    7320
```

```
atctggacga agagcatcag gggctcgcgc cagccgaact gttcgccagg ctcaaggcgc    7380
gcatgcccga cggcgatgat ctcgtcgtga cccatggcga tgcctgcttg ccgaatatca    7440
tggtggaaaa tggccgcttt tctggattca tcgactgtgg ccggctgggt gtggcggacc    7500
gctatcagga catagcgttg gctacccgtg atattgctga agagcttggc ggcgaatggg    7560
ctgaccgctt cctcgtgctt tacggtatcg ccgctcccga ttcgcagcgc atcgccttct    7620
atcgccttct tgacgagttc ttctgagggg atccgctgta agtctgcaga aattgatgat    7680
ctattaaaca ataaagatgt ccactaaaat ggaagttttt cctgtcatac tttgttaaga    7740
agggtgagaa cagagtacct acattttgaa tggaaggatt ggagctacgg gggtgggggt    7800
ggggtgggat tagataaatg cctgctcttt actgaaggct ctttactatt gctttatgat    7860
aatgtttcat agttggatat cataaattta acaagcaaaa ccaaattaag ggccagctca    7920
ttcctcccac tcatgatcta tagatctata gatctctcgt gggatcattg ttttttctctt    7980 gattcccact ttgtggttct aagtactgtg gtttccaaat gtgtcagttt catagcctga    8040
agaacgagat cagcagcctc tgttccacat acacttcatt ctcagtattg ttttgccaag    8100
ttctaattcc atcagaaagc ttgcagaaga tctccccaac tggggtaacc tttgagttct    8160
ctcagttggg gggcgcgcc ggctagaaga tgggcgggag tcttctgggc aggcttaaag    8220
gctaacctgg tgtgtgggcg ttgtcctgca ggggaattga acaggtgtaa aattggaggg    8280
acaagacttc ccacagattt tcggttttgt cgggaagttt tttaataggg gcaaataagg    8340
aaaatgggag gataggtagt catctggggt tttatgcagc aaaactacag gttattattg    8400
cttgtgatcc gcctcggagt attttccatc gaggtagatt aaagacatgc tcacccgagt    8460
tttatactct cctgcttgag atccttacta cagtatgaaa ttacagtgtc gcgagttaga    8520
ctatgtaagc agaattttaa tcatttttaa agagcccagt acttcatatc catttctccc    8580
gctccttctg cagccttatc aaaaggtatt ttagaacact catttagcc ccattttcat    8640 ttattatact ggcttatcca acccctagac agagcattgg catttttccct ttcctgatct    8700 tagaagtctg atgactcatg aaaccagaca gattagttac atacaccaca aatcgaggct    8760
gtagctgggg cctcaacact gcagttcttt tataactcct tagtacactt tttgttgatc    8820 cttttgccttg atccttaatt ttcagtgtct atcacctctc ccgtcaggtg gtgttccaca    8880
tttgggccta ttctcagtcc agggagtttt acaacaatag atgtattgag aatccaacct    8940
aaagcttaac tttccactcc catgaatgcc tctctccttt ttctccattt ataaactgag    9000
ctattaacca ttaatggttt ccaggtggat gtctcctccc ccaatattac ctgatgtatc    9060
ttacatattg ccaggctgat atttttaagac attaaaaggt atatttcatt attgagccac    9120
atggtattga ttactgctta ctaaaatttt gtcattgtac acatctgtaa aaggtggttc    9180
cttttggaat gcaaagttca ggtgtttgtt gtctttcctg acctaaggtc ttgtgagctt    9240 gtatttttttc tatttaagca gtgctttctc ttggactggc ttgactcatg gcattctaca    9300
cgttattgct ggtctaaatg tgattttgcc aagcttcttc aggacctata attttgcttg    9360
acttgtagcc aaaacaaagt aaaatgatta agcaacaaat gtatttgtga agcttggttt    9420
ttaggttgtt gtgttgtgtg tgcttgtgct ctataataat actatccagg ggctggagag    9480
gtggctcgga gttcaagagc acagactgct cttccagaag tcctgagttc aattcccagc    9540
aaccacatgg tggctcacaa ccatctgtaa tgggatctga tgccctcttc tggtgtgtct    9600
gaagaccaca agtgtattca cattaaataa ataaatcctc cttcttcttc tttttttttt    9660
```

```
tttaaagag aatactgtct ccagtagaat ttactgaagt aatgaaatac tttgtgtttg    9720
ttccaatatg gtagccaata atcaaattac tctttaagca ctggaaatgt taccaaggaa    9780
ctaattttta tttgaagtgt aactgtggac agaggagcca taactgcaga cttgtgggat    9840
acagaagacc aatgcagact ttaatgtctt ttctcttaca ctaagcaata aagaaataaa    9900
aattgaactt ctagtatcct atttgtttaa actgctagct ttacttaact tttgtgcttc    9960
atctatacaa agctgaaagc taagtctgca gccattacta aacatgaaag caagtaatga   10020
taattttgga tttcaaaaat gtagggccag agtttagcca gccagtggtg gtgcttgcct   10080
ttatgccttt aatcccagca ctctggaggc agagacaggc agatctctga gtttgagccc   10140
agcctggtct acacatcaag ttctatctag gatagccagg aatacacaca gaaaccctgt   10200
tggggagggg ggctctgaga tttcataaaa ttataattga agcattccct aatgagccac   10260
tatggatgtg gctaaatccg tctacctttc tgatgagatt tgggtattat ttttctgtc   10320 tctgctgttg gttgggtctt ttgacactgt gggctttctt taaagcctcc ttcctgccat   10380
gtggtctctt gtttgctact aacttcccat ggcttaaatg gcatggcttt ttgccttcta   10440
agggcagctg ctgagatttg cagcctgatt tccagggtgg ggttgggaaa tctttcaaac   10500
actaaaattg tcctttaatt tttttttaa aaaatgggtt atataataaa cctcataaaa   10560
tagttatgag gagtgaggtg gactaatatt aaatgagtcc ctccctata aaagagctat   10620 taaggctttt tgtcttatac ttaactttt ttttaaatgt ggtatcttta gaaccaaggg   10680
tcttagagtt ttagtataca gaaactgttg catcgcttaa tcagattttc tagtttcaaa   10740
tccagagaat ccaaattctt cacagccaaa gtcaaattaa gaatttctga cttttaatgt   10800
taatttgctt actgtgaata taaaaatgat agcttttcct gaggcagggt ctcactatgt   10860
atctctgcct gatctgcaac aagatatgta gactaaagtt ctgcctgctt ttgtctcctg   10920
aatactaagg ttaaaatgta gtaatacttt tggaacttgc aggtcagatt cttttatagg   10980
ggacacacta agggagcttg ggtgatagtt ggtaaaatgt gtttcaagtg atgaaaactt   11040
gaattattat caccgcaacc tacttttaa aaaaaaagc caggcctgtt agagcatgct   11100
taagggatcc ctaggacttg ctgagcacac aagagtagtt acttggcagg ctcctggtga   11160
gagcatattt caaaaaacaa ggcagacaac caagaaacta cagttaaggt tacctgtctt   11220
taaaccatct gcatatacac agggatatta aaatattcca aataatattt cattcaagtt   11280
ttcccccatc aaattgggac atggatttct ccggtgaata ggcagagttg gaaactaaac   11340
aaatgttggt tttgtgattt tgtgaaattgt tttcaagtga tagttaaagc ccatgagata   11400
cagaacaaag ctgctatttc gaggtctctt ggtttatact cagaagcact tctttgggtt   11460
tccctgcact atcctgatca tgtgctaggc ctacctagg ctgattgttg ttcaaataaa   11520
cttaagtttc ctgtcaggtg atgtcatatg atttcatata tcaaggcaaa acatgttata   11580
tatgttaaac atttgtactt aatgtgaaag ttaggtcttt gtgggtttga ttttaatt   11640 tcaaaacctg agctaaataa gtcattttta catgtcttac atttggtgga attgtataat   11700
tgtggtttgc aggcaagact ctctgaccta gtaaccctac ctatagagca ctttgctggg   11760
tcacaagtct aggagtcaag catttcacct tgaagttgag acgttttgtt agtgtatact   11820
agtttatatg ttggaggaca tgtttatcca gaagatattc aggactattt ttgactgggc   11880
taaggaattg attctgatta gcactgttag tgagcattga gtggccttta ggcttgaatt   11940
ggagtcactt gtatatctca aataatgctg gccttttta aaaagccctt gttctttatc   12000
accctgtttt ctacataatt tttgttcaaa gaaatacttg tttggatctc cttttgacaa   12060
```

```
caatagcatg ttttcaagcc atatttttt tccttttttt tttttttttt ggttttcga    12120 gacagggttt ctctgtatag ccctggctgt cctggaactc actttgtaga ccaggctggc   12180
ctcgaactca gaaatccgcc tgcctctgcc tcctgagtgc cgggattaaa ggcgtgcacc   12240
accacgcctg gctaagttgg atattttgtt atataactat aaccaatact aactccactg   12300
ggtggatttt taattcagtc agtagtctta agtggtcttt attggcccctt cattaaaatc   12360 tactgttcac tctaacagag gctgttggta ctagtggcac ttaagcaact tcctacggat   12420
atactagcag attaagggtc aggatagaa actagtctag cgttttgtat acctaccagc    12480
tttatactac cttgttctga tagaaatatt tcaggacatc tagcttatcg ataccgtcga   12540
cggtatcgat aagcttgata tcgaattcta ccgggtaggg gaggcgcttt tcccaaggca   12600
gtctggagca tgcgctttag cagccccgct gggcacttgg cgctacacaa gtggcctctg   12660
gcctcgcaca cattccacat ccaccggtag cgccaaccg gctccgttct ttggtggccc    12720
cttcgcgcca ccttctactc ctcccctagt caggaagttc cccccgccc cgcagctcgc    12780 gtcgtgcagg acgtgacaaa tggaagtagc acgtctcact agtctcgtgc agatggacag   12840
caccgctgag caatggaagc gggtaggcct ttggggcagc ggccaatagc agctttgctc   12900
cttcgctttc tgggctcaga ggctgggaag gggtgggtcc ggggcgggc tcaggggcgg    12960 gctcaggggc gggcgggcg cccgaaggtc ctccggaggc ccggcattct gcacgcttca    13020
aaagcgcacg tctgccgcgc tgttctcctc ttcctcatct ccgggccttt cgacctgcag   13080
gtcctcgcca tggatcctga tgatgttgtt gattcttcta aatcttttgt gatggaaaac   13140
ttttcttcgt accacgggac taaacctggt tatgtagatt ccattcaaaa aggtatacaa   13200
aagccaaaat ctggtacaca aggaaattat gacgatgatt ggaaagggtt ttatagtacc   13260
gacaataaat acgacgctgc gggatactct gtagataatg aaaacccgct ctctggaaaa   13320
gctggaggcg tggtcaaagt gacgtatcca ggactgacga aggttctcgc actaaaagtg   13380
gataatgccg aaactattaa gaaagagtta ggtttaagtc tcactgaacc gttgatggag   13440
caagtcggaa cggaagagtt tatcaaaagg ttcggtgatg gtgcttcgcg tgtagtgctc   13500
agccttccct tcgctgaggg gagttctagc gttgaatata ttaataactg gaacaggcg    13560 aaagcgttaa gctagaact tgagattaat tttgaaaccc gtggaaaacg tggccaagat    13620
gcgatgtatg agtatatggc tcaagcctgt gcaggaaatc gtgtcaggcg atctctttgt   13680
gaaggaacct tacttctgtg gtgtgacata attggacaaa ctacctacag agatttaaag   13740
ctctaaggta aatataaaat ttttaagtgt ataatgtgtt aaaactactga ttctaattgt   13800 ttgtgtattt tagattccaa cctatggaac tgatgaatgg gagcagtggt ggaatgcaga   13860
tcctagagct cgctgatcag cctcgactgt gccttctagt tgccagccat ctgttgtttg   13920
cccctccccc gtgccttcct tgaccctgga aggtgccact cccactgtcc tttcctaata   13980
aaatgaggaa attgcatcgc attgtctgag taggtgtcat tctattctgg ggggtggggt   14040
ggggcaggac agcaagggg aggattggga agacaatagc aggcatgctg gggatgcggt    14100
gggctctatg gcttctgagg cggaaagaac cagctgggc tcgagggggg gcccggtacc    14160
cagcttttgt tccctttagt gagggttaat tgcgcgcttg gcgtaatcat ggtcatagct   14220
gtttcctgtg tgaaattgtt atccgctcac aattccacac aacatacgag ccggaagcat   14280
aaagtgtaaa gcctggggtg cctaatgagt gagctaactc acattaattg cgttgcgctc   14340
actgcccgct ttccagtcgg gaaacctgtc gtgccagctg cattaatgaa tcggccaacg   14400
```

```
cgcggggaga ggcggtttgc gtattgggcg ctcttccgct tcctcgctca ctgactcgct    14460
gcgctcggtc gttcggctgc ggcgagcggt atcagctcac tcaaaggcgg taatacggtt    14520
atccacagaa tcagggqata acgcaggaaa gaacatgtga gcaaaaggcc agcaaaaggc    14580
caggaaccgt aaaaaggccg cgttgctggc gtttttccat aggctccgcc ccctgacga    14640 gcatcacaaa aatcgacgct caagtcagag gtggcgaaac ccgacaggac tataaagata    14700
ccaggcgttt ccccctggaa gctccctcgt gcgctctcct gttccgaccc tgccgcttac    14760
cggatacctg tccgccttc tcccttcggg aagcgtggcg ctttctcata gctcacgctg    14820
taggtatctc agttcggtgt aggtcgttcg ctccaagctg ggctgtgtgc acgaaccccc    14880
cgttcagccc gaccgctgcg ccttatccgg taactatcgt cttgagtcca acccggtaag    14940
acacgactta tcgccactgg cagcagccac tggtaacagg attagcagag cgaggtatgt    15000
aggcggtgct acagagttct tgaagtggtg gcctaactac ggctacacta agaacagt    15060 atttggtatc tgcgctctgc tgaagccagt taccttcgga aaaagagttg gtagctcttg    15120
atccggcaaa caaccaccg ctggtagcgg tggtttttt gtttgcaagc agcagattac    15180
gcgcagaaaa aaaggatctc aagaagatcc tttgatcttt tctacggggt ctgacgctca    15240
gtggaacgaa aactcacgtt aagggatttt ggtcatgaga ttatcaaaaa ggatcttcac    15300
ctagatcctt ttaaattaaa aatgaagttt taaatcaatc taaagtatat atgagtaaac    15360
ttggtctgac agttaccaat gcttaatcag tgaggcacct atctcagcga tctgtctatt    15420
tcgttcatcc atagttgcct gactccccgt cgtgtagata actacgatac gggagggctt    15480
accatctggc cccagtgctg caatgatacc gcgagaccca cgctcaccgg ctccagattt    15540
atcagcaata aaccagccag ccggaagggc cgagcgcaga agtggtcctg caactttatc    15600
cgcctccatc cagtctatta attgttgccg ggaagctaga gtaagtagtt cgccagttaa    15660
tagtttgcgc aacgttgttg ccattgctac aggcatcgtg gtgtcacgct cgtcgtttgg    15720
tatggcttca ttcagctccg gttcccaacg atcaaggcga gttacatgat cccccatgtt    15780
gtgcaaaaaa gcggttagct ccttcggtcc tccgatcgtt gtcagaagta agttggccgc    15840
agtgttatca ctcatggtta tggcagcact gcataattct cttactgtca tgccatccgt    15900
aagatgcttt tctgtgactg gtgagtactc aaccaagtca ttctgagaat agtgtatgcg    15960
gcgaccgagt tgctcttgcc cggcgtcaat acgggataat accgcgccac atagcagaac    16020
tttaaaagtg ctcatcattg gaaaacgttc ttcggggcga aaactctcaa ggatcttacc    16080
gctgttgaga tccagttcga tgtaacccac tcgtgcaccc aactgatctt cagcatcttt    16140
tactttcacc agcgtttctg ggtgagcaaa aacaggaagg caaaatgccg caaaaaaggg    16200
aataagggcg acacggaaat gttgaatact catactcttc cttttcaat attattgaag    16260 catttatcag ggttattgtc tcatgagcgg atacatattt gaatgtattt agaaaaataa    16320
acaaataggg gttccgcgca catttccccg aaaagtgcca cctaaattgt aagcgttaat    16380
attttgttaa aattcgcgtt aaattttgt taatcagct cattttttaa ccaataggcc    16440
gaaatcggca aaatccctta taaatcaaaa gaatagaccg agatagggtt gagtgttgtt    16500
ccagtttgga acaagagtcc actattaaag aacgtggact ccaacgtcaa agggcgaaaa    16560
accgtctatc agggcgatgg cccactacgt gaaccatcac cctaatcaag ttttttgggg    16620
tcgaggtgcc gtaaagcact aaatcggaac cctaaaggga gcccccgatt tagagcttga    16680
cggggaaagc cggcgaacgt ggcgagaaag gaagggaaga agcgaaagg agcgggcgct    16740 agggcgctgg caagtgtagc ggtcacgctg cgcgtaacca ccacacccgc cgcgcttaat    16800
```

```
gcgccgctac agggcgcgtc ccattcgcca ttcaggctgc gcaactgttg ggaagggcga    16860
tcggtgcggg cctcttcgct attacgccag ctggcgaaag ggggatgtgc tgcaaggcga    16920
ttaagttggg taacgccagg gttttcccag tcacgacgtt gtaaaacgac ggccagtgag    16980
cgcgcgtaat acgactcact atagggcgaa ttggagctcc a                       17021
```